(12) United States Patent
Chen et al.

(10) Patent No.: US 9,925,235 B2
(45) Date of Patent: Mar. 27, 2018

(54) TILAPIA PISCIDINS FOR USE IN ENHANCEMENT OF WOUND HEALING

(71) Applicants: Academia Sinica, Taipei (TW); National Taiwan Ocean University, Keelung (TW)

(72) Inventors: Jyh-Yih Chen, Ilan (TW); Chang-Jer Wu, Ilan (TW)

(73) Assignees: ACADEMIA SINICA, Taipei (TW); NATIONAL TAIWAN OCEAN UNIVERSITY, Keelung (TW)

( * ) Notice: Subject to any disclaimer, the term of this patent is extended or adjusted under 35 U.S.C. 154(b) by 0 days.

(21) Appl. No.: 15/137,281

(22) Filed: Apr. 25, 2016

(65) Prior Publication Data

US 2016/0310564 A1  Oct. 27, 2016

Related U.S. Application Data

(60) Provisional application No. 62/152,381, filed on Apr. 24, 2015.

(51) Int. Cl.
| | | |
|---|---|---|
| *A61K 38/16* | (2006.01) | |
| *A61K 38/17* | (2006.01) | |
| *C07K 14/00* | (2006.01) | |
| *C07K 4/12* | (2006.01) | |

(52) U.S. Cl.
CPC .................. *A61K 38/1706* (2013.01)

(58) Field of Classification Search
CPC .... A61K 38/1706; A61K 38/16; A61K 38/17; A61K 39/085; C07K 14/00; C07K 4/12
USPC ............... 514/2.4, 2.7, 21.4; 530/326, 388.4
See application file for complete search history.

(56) References Cited

U.S. PATENT DOCUMENTS

2017/0044222 A1*  2/2017  Alexander ....... A61K 47/48992

OTHER PUBLICATIONS

Peng et al., "Five Different Piscidins from Nile Tilapia, *Oreochromis niloticus*: Analysis of Their Expressions and Biological Functions," PLOS One, Nov. 30, 2012, 7(11): 1-12.*
*Staphylococcus aureus* Infections from Merck Manual, pp. 1-6. Accessed Mar. 29, 2017.*

* cited by examiner

*Primary Examiner* — Julie Ha
(74) *Attorney, Agent, or Firm* — Juan Carlos A. Marquez; Marquez IP Law Office, PLLC

(57) ABSTRACT

A method for enhancing wound healing or treating methicillin-resistant *Staphylococcus aureus* (MRSA) infection in a wound comprising administering a subject in need thereof with a therapeutically effective amount of a tilapia piscidin (TP) is described, wherein the TP is preferably TP3 or TP4.

3 Claims, 18 Drawing Sheets

Collagen I keratin 10

TILAPIA PISCIDINS FOR USE IN ENHANCEMENT OF WOUND HEALING

RELATED APPLICATION

The present application claims priority under 35 U.S.C. § 119(e) to U.S. Provisional Patent Application No. 62/152,381, filed Apr. 24, 2015, the content of which is herein incorporated by reference in its entirety.

FIELD OF THE INVENTION

The present invention relates to a new medicament for wound healing, particularly in treatment for MRSA infections in wounds.

BACKGROUND OF THE INVENTION

The discovery of antibiotics has been one of the greatest achievements of modern medicine. However, antibiotic resistance is recognized as a major problem worldwide in the management of infectious disease, both in hospital settings and in the community. However, wound infection due to multidrug resistant organisms, such as methicillin-resistant *Staphylococcus aureus* (MRSA) continues to increase.

Methicillin-resistant *Staphylococcus aureus* (MRSA) is a major cause of infection in injured patients, and healthcare associated (HA) and community associated (CA) MRSA have become prevalent in recent years. Its emergence is a consequence of excessive use of certain antibiotics. MRSA generally does not cause infection in the absence of injury. When MRSA enters the body through a cut or abrasion, it may cause infection by evading the natural protective mechanisms of the body. This necessitates the use of alternative therapies, which ideally do not result in resistance through continuous selective pressure. MRSA infections in recent years have been treated with mupirocin, clindamycin, trimethoprim/sulfamethoxazole, doxycycline, minocycline, linezolid, vancomycin, daptomycin, and telavancin [Bjorn et al., Anti-infectious and anti-inflammatory effects of peptide fragments sequentially derived from the antimicrobial peptide centrocin 1 isolated from the green sea urchin, *Strongylocentrotus droebachiensis*. AMB Express 2012, 2:67]. Also, vancomycin, linezolid, daptomycin (Cubicin), tigecycline (Tygacil), and telavancin (Vibativ) were reported to treat severe MRSA infections of skin and soft tissue in hospitals. Vancomycin, the primary treatment for MRSA, possessed high minimum inhibitory concentration (MIC) values and other limitations [Palazzolo-Ballance et al., Neutrophil microbicides induce a pathogen survival response in community-associated methicillin-resistant *Staphylococcus aureus*. J Immunol 2008, 180:500-9].

Cationic gene-encoded host defense peptides (HDP) are nature's most diverse and lavish class of antibiotics. A subclass of HDP, known as antimicrobial peptides (AMP), exerts direct antimicrobial activity. Antimicrobial peptides (AMPs) are part of the host defense system of a wide range of invertebrates, plants, and animals [Lee et al., A helix-PXXP-helix peptide with antibacterial activity without cytotoxicity against MDRPA-infected mice. Biomaterials. 2014; 35:1025-1039; Wimley & Hristova, Antimicrobial peptides: successes, challenges and unanswered questions. The Journal of membrane biology. 2011; 239:27-34]. AMPs typically show potent antimicrobial activity against a broad range of bacteria, virus, fungi, and protozoans. The key features of AMPs are that they are short, amphipathic, and cationic, they possess rapid killing ability, and they target the membrane and internal components of the cell [Brogden, Antimicrobial peptides: pore formers or metabolic inhibitors in bacteria, Nature reviews Microbiology. 2005; 3:238-250; Yount & Yeaman, Immunocontinuum: perspectives in antimicrobial peptide mechanisms of action and resistance. Protein and peptide letters. 2005; 12:49-67; Yeaman & Yount, Mechanisms of antimicrobial peptide action and resistance. Pharmacological reviews. 2003; 55:27-55; Hancock & Scott, The role of antimicrobial peptides in animal defenses. Proceedings of the National Academy of Sciences of the United States of America. 2000; 97:8856-8861].

Piscidin AMPs were found to be made up of 21~44 residues and possess an amphipathic-helical structure [Maisetta et al., In Vitro Bactericidal Activity of Human β-Defensin 3 against Multidrug-Resistant Nosocomial Strains. Antimicrobial Agents and Chemotherapy 2006; 50:806-809; Winkler et al., Unexpected Challenges in Treating 432 Multidrug-resistant Gram-negative Rods: Resistance to Ceftazidime-Avibactam in Archived Isolates of Pseudomonas aeruginosa. Antimicrob Agents Chemother 2014]. In 2012, five new piscidins, named tilapia piscidins 1~5 (TP1~5), were isolated from Nile tilapia (*Oreochromis niloticus*) [Peng et al., Five Different Piscidins from Nile Tilapia, *Oreochromis niloticus*: Analysis of Their Expressions and Biological Functions. PloS ONE 2012; 7(11): e50263].

However, there is still a need to develop a new therapy or new therapeutics for wound healing, particular for treating MRSA infections in wounds.

SUMMARY OF THE INVENTION

It is unexpectedly found that five piscidins isolated from Tilapia have antimicrobial activity, revealing that these peptides are potent and promising a therapeutic agent in would healing, particularly MRSA infection in wounds.

In one aspect, the invention provides method for wound healing comprising administering a subject in need thereof with a therapeutically effective amount of a tilapia piscidin.

In another aspect, the invention provides a method for preventing or treating methicillin-resistant *Staphylococcus aureus* (MRSA) infection in wounds, comprising administering a subject in need thereof with a therapeutically effective amount of a tilapia piscidin.

In one further aspect, the invention provides a composition or pharmaceutical composition for preventing or treating MRSA infection in wounds.

In one yet aspect, the invention provides a use of a TP for manufacturing a medicament for preventing or treating MRSA infections in wounds.

In one embodiment of the invention, the TP is selected from the group consisting of TP1, TP2, TP3, TP4, TP5 and combination thereof.

In one particular example of the invention, the TP is TP3 or TP4

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

In FIG. 1A-1C, BHK-21 cells were treated with different doses of TP3 for 24 h; and the cell viability was measured by neutral red, LDH and MTT assay, respectively. (r=3; n=6). In FIG. 1D, MRSA was cultured in different concentrations of TP3; and relative bacterial proliferation was determined based on optical density at 600 nm. (r=3; n=6). Values with different letters show significant differences (p<0.05), as determined by ANOVA.

FIG. 2A shows that the mice were injected with MRSA ($1 \times 10^6$ cfu/mouse), and independent groups (n=5) were subsequently injected with TP3, vanomycin and methicillin. The survival rate was monitored on a daily basis for up to 8 days.

FIG. 3A shows that the all full-thickness aseptic wounds closed by day. Meth., methicillin; Vanc., vancomycin. FIG. 3B shows that the full-thickness wounds contaminated with microorganisms increased in size initially, while TP3 treated wounds did not exhibit the initial expansion and closed somewhat faster (day) than vancomycin-treated wounds.

FIG. 4A-4C show that TP3 modulated gene expression profiles in mice. Adult mice were treated with TP3 and antibiotics in MRSA infected mice, while controls were untreated. After different day, total RNA was isolated from the wound and reverse transcribed for use in real-time qPCR analysis TNF-a (FIG. 4A), IL-6 (FIG. 4B) and CXCL5 (FIG. 4C) gene expression. R>3; n>3. Values with different symbols show significant differences (P<0.05), as determined by ANOVA. (*, P<0.05; **, P<0.01; n.s.: not significant)

In FIG. 5A-5C, Hs-68 cells were treated with different doses of TP4 for 48 h, and cell viability was measured by neutral red, LDH, and MTT assays. (r=3; n=6.) In FIG. 5D-5F, the experimental Hs-68 cells were treated with TP4 (6.25 m/ml), while control cells were untreated. After 48 h, total RNA was isolated and reverse transcribed for use in real-time qPCR analysis. Six replicate wells were analyzed per assay. Results represent the mean±SEM from three independent experiments. (Student's t-test: *, P<0.05; **, P<0.01; n.s.: not significant).

In FIG. 6A-6C, HaCaT cells were treated with different doses of TP4 for 48 h, and cell viability was measured by neutral red, LDH, and MTT assays (r=3; n=6). In FIGS. 6D and 6E, thee experimental HaCaT cells were treated with TP4 (6.25 µg/ml), while control cells were untreated. After 48 h, total RNA was isolated and reverse transcribed for use in real-time qPCR analysis. Six replicate wells were analyzed per assay. Results represent the mean±SEM from three independent experiments. (Student's t-test: *, P<0.05; **, P<0.01, n.s.: not significant).

In FIG. 7A, mice were injected with MRSA ($1 \times 10^6$ cfu/mouse), and independent groups (n=10) were subsequently injected with TP4, vancomycin, or methicillin. The survival rate was monitored on a daily basis for up to 8 days. In FIG. 7B, to determine curative potential, mice were first injected with MRSA ($1 \times 10^6$ cfu/mouse) and then with TP4 (0.005 mg/g) 10, 60, 120, or 180 min later. At these injection times, the MRSA experimental groups exhibited survival rates of 100%, 80%, 60%, and 50%, respectively.

FIG. 8A shows the all full-thickness aseptic wounds closed by day 25. Meth., methicillin; Vanc., vancomycin. FIG. 8B shows the full-thickness wounds contaminated with microorganisms increased in size initially, while TP4-treated wounds did not exhibit the initial expansion and closed somewhat faster (day 21) than vancomycin-treated wounds.

DETAILED DESCRIPTION OF THE INVENTION

Figure 1A:
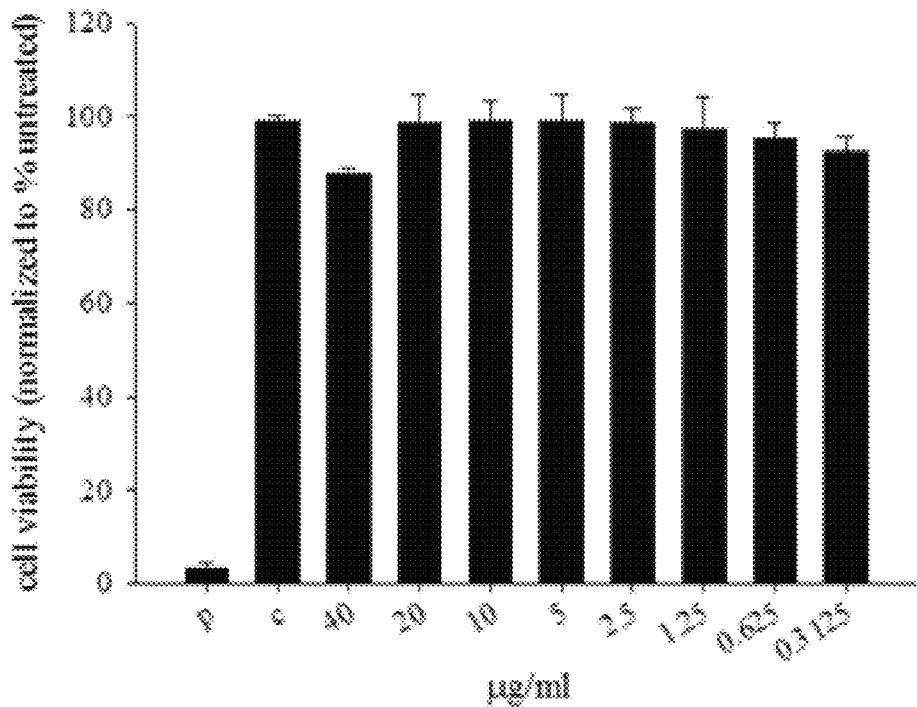
FIG. 1A-1D show the cytotoxicity of tilapia piscidin 3 (TP3) in baby hamster kidney cells (BHK-21) and antibacterial activity.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

Tilapia Piscidins

As disclosed in Peng et al., *Oreochromis niloticus* spleen tissues were collected for RNA extraction and the Nile tilapia piscidin coding region was amplified by a polymerase chain reaction (PCR) using GR649653.1 (named TP1). GR604642.1 (XM 003456635; named TP2), GR645750.1 (XM 003456614; named TP3), GR634176.1 (XM 003456613; named TP4), and GR648328.1 (named TP5) from PubMed GenBank data. The following primers were used.

Primer sequences:

TP1
F-
ATGAAGTCTGCTGTGATCTTTCTTGTGC) (SEQ ID No: 1)

R-
CTAGTCAAATTCCCGTTGACGCA) (SEQ ID No: 2)

TP2
F-
ATGAAGTGTGCTGCAGTATTTCTTATGCTGTCC) (SEQ ID No: 3)

R-
CTAGTCAAAATTAAGTCGACGAGGGT) (SEQ ID No: 4)

TP3
F-
ATGAAGTGCACCATGCTGTTCCTTGTGCTGTCGATGGTT) (SEQ ID No: 5)

R-
CTAGTTAAAAGCAGCCCTTTCCC) (SEQ ID No: 6)

TP4
F-
ATGAAGTGCACTATACTGTTCCTTGTGCTGTCGATGGTG) (SEQ ID No: 7)

R-
CTAGTTAAAAGCAACTCTCTCGTTTG) (SEQ ID No: 8)

TP5
F-
ATGAAGTCTGCCATAATCTTTCTTGTAT) (SEQ ID No: 9)

R-
CTATGACATCACAGCATCTTCAAATTC) (SEQ ID No: 10)

The PCR products were cloned into a pCR-Blunt (Invitrogen, CA, USA) and transformed into the DH5α E. coli strain, and the recombinant clones were chosen to sequence and identify the tilapia piscidins.

Peptides of TP were synthesized by GL Biochem (Shanghai, China) using a solid-phase procedure of Fmoc chemistry. Crude peptides were extracted, lyophilized, and purified by reverse-phase high-performance liquid chromatography (HPLC). The molecular masses and purities of the purified peptides were respectively verified by mass spectroscopy and HPLC. Synthetic peptides at >95% purity were reconstituted in phosphate-buffered saline (PBS; pH 7.4) for the experiments. The amino acid sequences of Nile tilapia piscidins were obtained from the cloned cDNA:

Amino acid sequences:

TP1:
FDWDSVLKGVEGFVRGYF (SEQ ID No: 11)

TP2:
GECIWDAIFHGAKHFLHRLVNP (SEQ ID No: 12)

TP3:
FIHHIIGGLFSVGKHIHSLIHGH (SEQ ID No: 13)

TP4:
FIHHIIGGLFSAGKAIHRLIRRRRR (SEQ ID No: 14)

TP5:
QLQGKQVSGEVVQKVLQELIQSVAKP (SEQ ID No: 15)

The cDNA coding regions of five different piscidin sequences were isolated and characterized. The five cDNA sequences named TP1-5 respectively encoded 68, 77, 76, 89, and 64 amino acids. A potential cleavage site for the signal peptide was predicted to be between Pro19 and Gly20 for TP1 having an amino acid sequence as set forth in SEQ ID NO: 11, between Pro19 and Gly20 for TP2 having an amino acid sequence as set forth in SEQ ID NO: 12, between Pro19 and Gly20 for TP3 having an amino acid sequence as set forth in SEQ ID NO: 13, between Ala17 and Glu18 for TP4 having an amino acid sequence as set forth in SEQ ID NO: 14, and between Leu22 and Gln23 for TP5 having an amino acid sequence as set forth in SEQ ID NO: 15. In addition, it was found that one consensus nuclear localization sequence (NLS) in the Nile tilapia piscidin TP4 having an amino acid sequence as set forth in SEQ ID No: 14, located at amino acid number 43 (RRRR).

Tilapia Piscidin 3 (TP3)

Tilapia piscidin 3 (TP3) is an AMP isolated from Nile tilapia (Oreochromis niloticus), and was characterized. Tilapia piscidin 3 (TP3), is a 23-amino acid peptide that starts with phenylalanine (F) and ends with histidine (H) as set forth in SEQ ID NO: 13. TP3 is a pore forming peptide with an α-helix structure, which confers selective cytolytic activity against bacteria. In addition to disrupting bacterial membranes, Tilapia α-helix antimicrobial peptides have been reported to stimulate the immunogenicity, induce a TH1 cellular immune response, and as adjuvants to vaccine in fish [Acosta et al., Co-administration of tilapia alpha-helical antimicrobial peptides with subunit antigens boost immunogenicity in mice and tilapia (Oreochromis niloticus). Vaccine. 2014; 32:223-229]. TP3 has antimicrobial activity against both Gram-positive and -negative bacteria. Furthermore, clinical case studies have shown that application of antimicrobial peptides to severely infected cutaneous wounds can clear the infection and improve healing [O'Meara et al., S, Cullum N, Majid M and Sheldon T. Systematic reviews of wound care management: (3) antimicrobial agents for chronic wounds; (4) diabetic foot ulceration. Health Technol Assess. 2000; 4:1-237]. Thus, TP3 has many features consistent with antibiotics, but potentially has broader applications, and may avoid or reduce concerns of bacterial resistance.

Tilapia Piscidin 4 (TP4)

Tilapia piscidin 4 (TP4) is an AMP isolated from Nile tilapia (Oreochromis niloticus), and was characterized by Peng et al. Tilapia piscidin 4 (TP4) is a 23 amino acid peptide that starts with phenylalanine (F) and ends with histidine (H) as set forth in SEQ ID NO: 14. TP4 is a pore-forming peptide with an α-helix structure, which confers selective cytolytic activity against bacteria. In addition to disrupting bacterial membranes, Tilapia α-helix AMPs have been reported to stimulate immunogenicity, induce a TH1 cellular immune response, and act as adjuvants to vaccines in fish (Acosta et al.). TP4 has antimicrobial activity against both Gram-positive and -negative bacteria.

As evidenced in Example 1, TP3 provides antibiotic activity without inducing resistance, which is compatible with the use of antibiotics, and does not have any apparent immunotoxic effects. Given the prophylactic efficacy of TP3, and its inability to engender resistance, it may be suitable for situations in which there is a high risk of infection. It is concluded that TP3 is potent to be a good therapeutic agent for wound healing, as well as MRSA infections in wounds.

Furthermore, it is also demonstrated in Example 2 that TP4 provides antibiotic activity without inducing resistance, which is compatible with the use of antibiotics, and does not have any apparent immunotoxic effects. It was found that TP4 induced proliferation of epithelial cells, which may be due to altered gene expression of collagen I, collagen III, keratinocyte growth factor (KGF), and keratin 10. In addition to its host defense function and modulatory effect on the innate immune system, TP4 may play an important role in reducing the risk of infection. It is also concluded that TP4 is potent to be a good therapeutic agent for wound healing, as well as MRSA infections in wounds.

Accordingly, the invention provides a method for wound healing comprising administering a subject in need thereof with a therapeutically effective amount of a tilapia piscidin, particularly for preventing or treating methicillin-resistant *Staphylococcus aureus* (MRSA) infection in wounds.

TP is selected from the group consisting of TP1, TP2, TP3, TP4, TP5 and combination thereof. In one particular example of the invention, the TP is TP3 or TP4.

Also provided are a composition or pharmaceutical composition for preventing or treating MRSA infection in wounds, and a use of a TP for manufacturing a medicament for preventing or treating MRSA infections in wounds.

The term "therapeutically effective amount" as used herein refers to an amount of a drug or pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of the peptide, or functional variant thereof, may be formulated as a pharmaceutical composition for administration. Accordingly, the invention further provides a pharmaceutical composition comprising a therapeutically effective amount of the peptide and one or more pharmaceutically acceptable carriers, diluents, or excipients.

The carrier(s), diluent(s) or excipient(s) must be acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

According to the invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

In one example of the invention, the pharmaceutical composition for oral administration may be presented as discrete units such as capsules or tablets; powders or granules; solutions or suspensions, and the like. In one particular example, the pharmaceutical composition is in the form of tablets.

The present invention will now be described more specifically with reference to the following examples, which are provided for the purpose of demonstration rather than limitation.

EXAMPLES

Example 1 Efficacy Experiments for TP3

Materials and Methods
1.1 Cells and Mice
The Baby Hamster Kidney cell line (BHK-21) was cultured in Roswell park memorial institute media (RPMI-1640) supplemented with 10% heat inactivated fetal bovine sera. Balb/c female mice were used for the experiments. All mice were housed in cages under specific pathogen-free conditions, and given water and standard laboratory chow ad libitum during the experiments. All animal handing procedures were in accordance with National Taiwan Ocean University (NTOU) guidelines. All procedures were approved by the Animal Care and Use Committee of NTOU, Keelung, Taiwan.
1.2 Reagents
Hematoxylin-eosin (H&E) (Cat no. 105175, Merck, Darmstadt, Germany) and Giemsa stain solution (Cat no. 51811826, Sigma, Mo., USA) were used to determine histological. Antibodies against macrophages (Cat no. 550282, BD Biosciences, CA, USA), lymphocytes (CD3e) (Cat no. 550277, BD Biosciences, CA, USA), and CD8a (Cat no. 14008182, eBiosciences, CA, USA) were used for immunohistochemistry (IHC).
1.3 In Vitro Toxicity
Cells were cultured at a density of $5 \times 10^4$ cells per well in flat-bottomed 96-well plates, and supplemented with various combinations of AMPs. After 24 h, Cell viability was measured by neutral red, LDH and MTT assay, respectively.
1.4 Synthesis of the Tilapia Piscidin 3 Peptides and Bacteriostatic Analysis
TP3 Peptides were synthesized by GL Biochem (Shanghai, China) using a solid-phase procedure of Fmoc chemistry. Crude peptides were extracted, lyophilized, and purified by reverse-phase high-performance liquid chromatography (HPLC). The molecular masses and purities of the purified peptides were respectively verified by mass spectroscopy and HPLC. Synthetic peptides at >95% purity were reconstituted in phosphate-buffered saline (PBS; pH 7.4) for the experiments. The TP3 sequence was the sequence of FIH-HIIGGLFSVGKHIHSLIHGH (SEQ ID No: 13). The minimal inhibitory concentration (MIC) of the peptides were determined by a broth microdilution analysis based on an online method (≤http://cmdr.ubc.ca/bobh/methods/MODI-FIEDMIC.html≥; Hancock Laboratory Methods. Department of Microbiology and Immunology, University of British Columbia, British Columbia, Canada) without modification.
1.5 In Vivo Toxicity
To determine the toxicity of TP3, TP3 was dissolved in phosphate-buffered saline (PBS; pH 7.4) and administered as intramuscular bolus injections in the left thigh (2 mg/mouse). Mice were observed for signs of systemic toxicity. To study the effect of treatment on biochemistry, mice (n=6 in each group) were treated with PBS (control). Blood samples (0.2 ml) were collected day 1, 3 and 6 after the final injection of TP3, and used to determine the serum levels of glutamic oxaloacetic transaminase (GOT), glutamic pyruvic transaminase (GPT), blood urea nitrogen (BUN), creatinine (CRE), total glucose (GLU), and creatine phosphokinase (CPK).

1.6 Therapeutic Use in a Mouse Model of MRSA Sepsis

Female Balb/c mice (6-8 weeks old) were injected intraperitoneally with $10^6$ CFU MRSA per mouse. Ten minutes after MRSA injection, mice were injected intraperitoneally with vancomycin (0.01 mg/g mouse body weight), methicilin (0.01 mg/g mouse body weight), or TP3 (0.005 mg/g mouse body weight). In a second set of experiments, mice were given intraperitoneal injections of TP3 (0.005 mg/g mouse body weight) at 10, 60, 120, or 180 min after MRSA injection. The survival rate and status were recorded every 24 h for up to 192 h. To examine bacterial dissemination, mice were sacrificed at 48 h after injection with antibiotics or TP3, and the bacterial numbers in blood, peritoneum, spleen, liver, and mesenteric lymph nodes were recorded. Colony counts from the diluted bacterial solutions were expressed relative to those at the start of treatment. These experiments consisted of four groups, and each group contained 5 mice.

1.7 Mouse Models for Wound Healing

Female Balb/c mice (6-8 weeks old) were used for wound healing experiments. All mice were housed individually to prevent fighting and further damage to the wounds, and they were provided with food and water ad libitum. Mice were maintained on a 12 h light: dark cycle at room temperature, and acclimatized to the environment for at least a week before use in experiments. All researchers wore caps, sterile gloves, gowns, and shoe covers when handling mice. Hair was removed from the back of the mice by shaving, and a full thickness wound (1 cm in diameter) was then created in the exposed region. Each wound was inoculated with 50 µl of broth mix containing $10^6$ cfu (colony forming units) of *S. aureus*. At 5 min after inoculation, 50 µl TP3 (2 mg/ml) in a total volume of 0.1 ml were applied. Thirty minutes after treatment, wounds were covered with Tegaderm (3M, St. Paul, Minn.) to maintain uniformity, and to prevent the mice from removing the treatments. Based on initial experiments, we examined the wounds at 0, 3, 5 and 19 days post-injury, so as not to disturb the infection. Such examinations captured the transitions from inflammatory to regenerative, and regenerative to resolving phases of wound healing. Animals were subsequently euthanized by $CO_2$ inhalation and the wounds assessed. Four individuals in each group were examined at each time point for each experiment. Each wound was measured and then removed from the animal, with unwounded skin taken from the contralateral dorsum as a control. Each biopsy was bisected with three sections being used for tensiometry and histology, and two sections for quantitative determination of microbial load. Wound healing studies were repeated in triplicate.

1.8 Wound Closure Measurements

Tracings were taken immediately after injury. For uncontaminated wounds, wound size was determined every second day. For contaminated wounds, mice were euthanized at days 3, 5, 19 and tracings of the wound edges were made. Wound areas were determined using the Macintosh Adobe Photoshop program, Histogram Analysis. The percentage of wound contraction was calculated as follows: % Wound contraction=(A0−At)/A0×100, where A0 is the original wound area, and At is the area of wound at the time of biopsy on every two days, accordingly.

1.9 Assessment of Wound Infection

Multidrug-resistant strains of *Staphylococcus aureus* commonly associated with human wound infections were selected to generate a polymicrobial solution. The MRSA strain is a clinical isolate from stool obtained from Taipei City Hospital (Heping Fuyou branch). The initial inoculum was prepared by culturing aerobic bacteria in Tryptic Soy Broth (TSB) overnight at 37° C. Broths were subsequently centrifuged at 1000 rpm for 15 min, and resuspended in TSB with 15% glycerol, or chopped meat extract with 15% glycerol (for aerobic bacteria). The concentration was adjusted to $10^6$ cfu/50 µl, and stored at −80° C. Prior to wound application, the broth mix containing $10^6$ cfu (colony forming units) of *S. aureus*. At 5 min after inoculation, 50 µl TP3 (2 mg/ml) in a total volume of 0.1 ml were applied. Thirty minutes after treatment, wounds were covered with Tegaderm (3M, St. Paul, Minn.) to maintain uniformity, and to prevent the mice from removing the treatments. Based on initial experiments, we examined the wounds at 0, 3, 5 and 19 days post-injury, so as not to disturb the infection. Such examinations captured the transitions from inflammatory to regenerative, and regenerative to resolving phases of wound healing. Animals were subsequently euthanized by $CO_2$ inhalation and the wounds assessed. Four individuals in each group were examined at each time point for each experiment. Each wound was measured and then removed from the animal, with unwounded skin taken from the contralateral dorsum as a control. Each biopsy was bisected with three sections being used for tensiometry and histology, and two sections for quantitative determination of microbial load. Wound healing studies were repeated in triplicate.

1.10 Wound Closure Measurements

Tracings were taken immediately after injury. For uncontaminated wounds, wound size was determined every second day. For contaminated wounds, mice were euthanized at days 3, 5, 19 and tracings of the wound edges were made. Wound areas were determined using the Macintosh Adobe Photoshop program, Histogram Analysis. The percentage of wound contraction was calculated as follows: % Wound contraction=(A0−At)/A0×100, where A0 is the original wound area, and At is the area of wound at the time of biopsy on every two days, accordingly.

1.11 Assessment of Wound Infection

Multidrug-resistant strains of *Staphylococcus aureus* commonly associated with human wound infections were selected to generate a polymicrobial solution. The MRSA strain is a clinical isolate from stool obtained from Taipei City Hospital (Heping Fuyou branch). The initial inoculum was prepared by culturing aerobic bacteria in Tryptic Soy Broth (TSB) overnight at 37° C. Broths were subsequently centrifuged at 1000 rpm for 15 min, and resuspended in TSB with 15% glycerol, or chopped meat extract with 15% glycerol (for aerobic bacteria). The concentration was adjusted to $10^6$ cfu/50 µl, and stored at −80° C. Prior to wound application, the bacterial stocks were re-mixed. Microbial load was determined by direct plating, followed by freeze-thaw and cfu enumeration, in parallel with inoculations. The inoculum was delivered by sterile pipettes to the center of open wounds. After euthanization (at day 0, 3, 5, or 19), two bisected tissue segments were used to determine microbial load using the protocol for human wound biopsy culture, as stated in the UPMC Clinical Microbiology Laboratory Procedure Manual. Tissue biopsies were weighed and placed in 1.5 ml of TSB, and then homogenized in a tissue grinder. A single drop of the homogenate was placed on the slide and Gram stained for rough assessment (if one or more bacteria are present within the oil immersion field, the expected count in the tissue is at least $10^5$ cfu/g). Serial dilutions (1:10 (0.1+0.9)) of the tissue homogenate were made using distilled water. The cfu/g of tissue was calculated as follows: cfu/g=plate count (1/dilution)×10/wt. of homogenized tissue.

1.12 Immunohistochemistry (IHC)

Skin tissues were removed and fixed as previously described. In brief, the cryosections were fixed with 4% formaldehyde, and the tissue samples were stained with hematoxylin/eosin, Giemsa, or Gram stain. IHC was analyzed by three independent investigators. Images were taken using a BX-51 microscope (Olympus, Japan).

1.13 Isolation of Messenger (m)RNA and Real-Time PCR

Total RNA was isolated from wound tissues and purified using a Qiagen RNeasy kit. Reverse transcription into cDNA was performed with iScript cDNA Synthesis Kits (BIO-RAD, USA) according to the manufacturer's recommendations. A real-time polymerase chain reaction (PCR) analysis was used to analyze the gene expressions, according to the manufacturer's instructions. The iQSYB® Green Supermix (BIO-RAD, USA) and specific primer pairs were used for selected genes, and a primer pair for GAPDH was used as the reference gene. A quantitative PCR was performed according to the following conditions: 40 cycles of 1 min at 95° C., 30 s at 55° C., and 1 min at 72° C. Using 0.5 ml of cDNA, 2× SYBR Green PCR Supermix, and 500 nM of the forward and reverse primers, the threshold cycle number (Ct) was calculated with BIO-RAD software. Relative transcript quantities were calculated using the ΔCt method with GAPDH as the reference gene that was amplified from the same samples. ΔCt is the difference in the threshold cycles of messenger (m)RNA for selected genes relative to those of GAPDH mRNA. The real-time PCR was performed in triplicate for each experimental group.

```
Primer sequences:

TNF-α:
F-
                                        (SEQ ID No: 16)
GGTGTTCATCCATTCTCTAC

R-
                                        (SEQ ID No: 17)
CCCAGCATCTTGTGTTTC

IL-6:
F-
                                        (SEQ ID No: 18)
TCCATCCAGTTGCCTTCTTG
```

```
Primer sequences:

R-
                                        (SEQ ID No: 19)
TTTCTCATTTCCACGATTTCCC

CXCL5:
F-
                                        (SEQ ID No: 20)
CTGACCCCAGTGAAGATAAG

R-
                                        (SEQ ID No: 21)
CCGATAGTGTGACAGATAGG

GAPDH:
F-
                                        (SEQ ID No: 22)
ACAATGAATACGGCTACAG

R-
                                        (SEQ ID No: 23)
GGTCCAGGGTTTCTTACT
```

1.14 Statistical Analysis

The experiments were conducted with three or more replicates, and repeated at least three times. Error bars represent the standard deviation. Histological and in vivo study results were representative of three independent experiments. A group of 7 mice was used for each treatment, and the experiment was repeated three times.

Results 1.15 In Vitro Toxicity and Efficacy of TP3

Figure 1B:
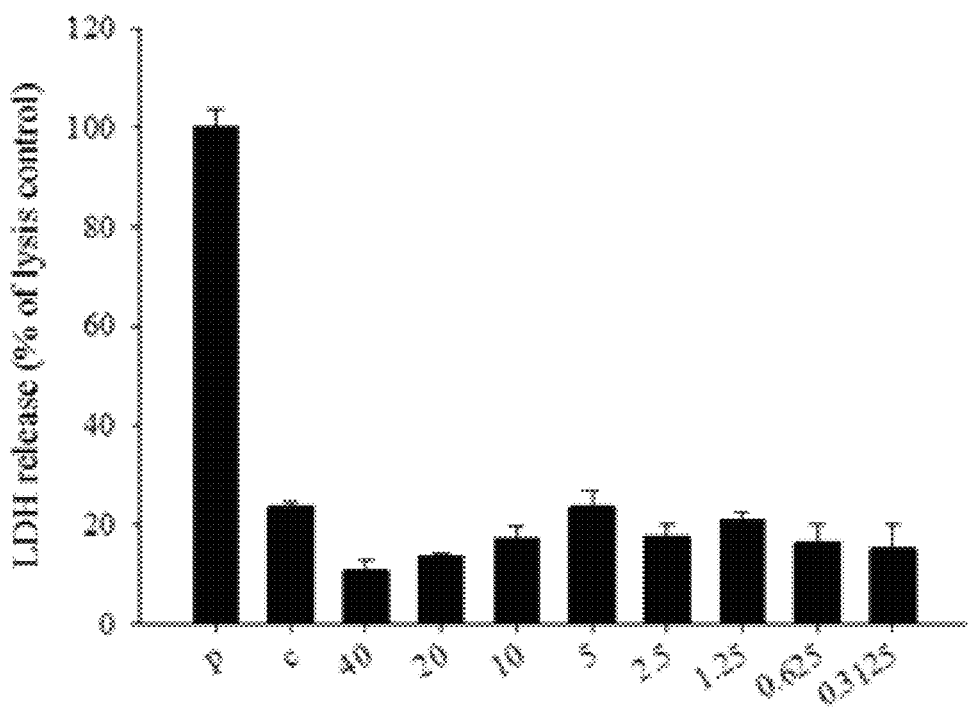
Figure 1C:
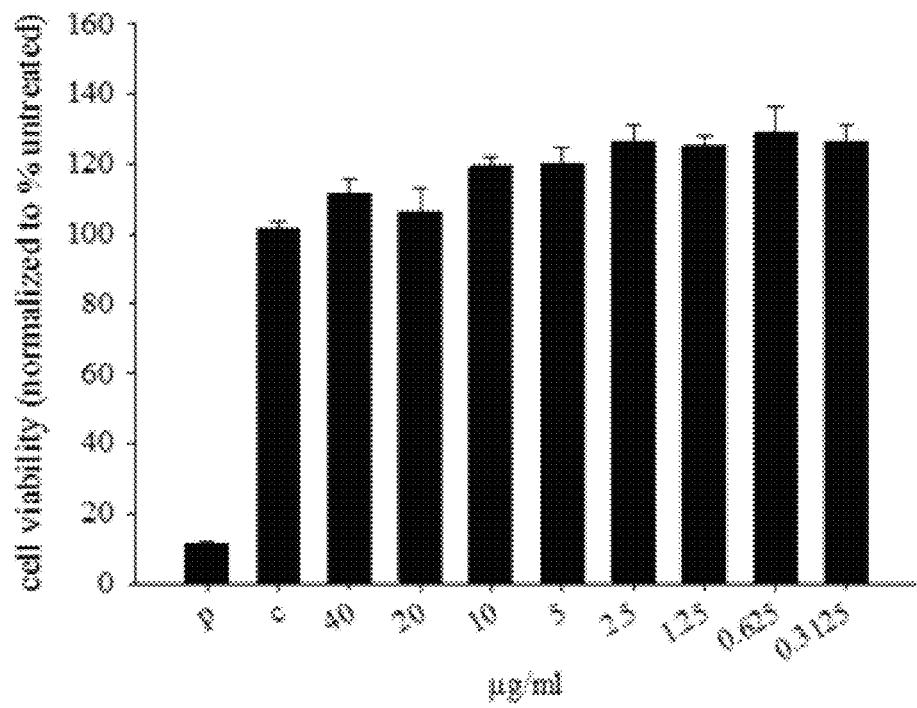
Figure 1D:
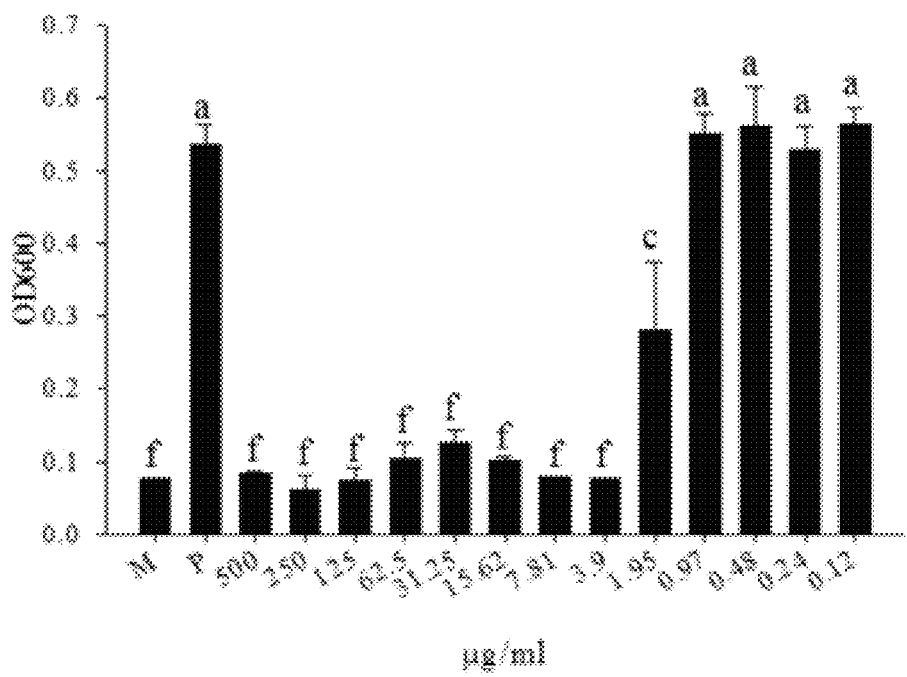

To evaluate the cell toxicity of TP3 in BHK-21 cells, the results of the cell toxicity assays measured by neutral red, LDH and MTT assay were shown in FIG. 1A-1C, TP3 at various concentrations up to 40 µg/ml did not affect cell viability. The minimal inhibitory concentration (MIC) for TP3 was >3.9 µg/ml against MRSA. Similarly, >3.9 µg/ml of TP3 effectively killed MRSA suspended in 10 mM sodium phosphate buffer, pH 7.2 (FIG. 1D).

1.16 TP3 Did Not Exert Acute Toxic Effects in Mice

The toxicity of TP3 was examined by delivering them via intramuscular (i.m.) injection into mice and measured of biochemical factors in the blood. Mice treated with 2 mg of TP3, did not induce any significant changes in the levels of glutamic oxaloacetic transaminase (GOT), glutamic pyruvic transaminase (GPT), blood urea nitrogen (BUN), creatinine (CRE), total glucose (GLU), or creatine phosphokinase (CPK) (Table 1).

TABLE 1

Biochemical parameters of mice after intramuscular injection of TP3 (2 mg/mouse)

| Time (day) | Control (n = 6) | | | TP3 (n = 6) | | |
|---|---|---|---|---|---|---|
| | 1 | 3 | 6 | 1 | 3 | 6 |
| GOT (U/l) | $45.6 \pm 3.7^A$ | $41.2 \pm 1.5^A$ | $45.6 \pm 3.7^A$ | $122.6 \pm 25.7^C$ | $47.3 \pm 5.9^A$ | $46 \pm 8.08^A$ |
| GPT (U/l) | $43.3 \pm 5.1^A$ | $46.4 \pm 4.3^A$ | $43.3 \pm 5.3^A$ | $71.3 \pm 8.6^C$ | $36.2 \pm 2.7^{AB}$ | $35 \pm 5.9^{AB}$ |
| CRE (mg/dl) | $0.4 \pm 0.1^A$ | $0.5 \pm 0.3^A$ | $0.5 \pm 0.1^A$ | $0.3 \pm 0.05^A$ | $0.41 \pm 0.04^A$ | $0.54 \pm 0.05^A$ |
| BUN (mg/dl) | $16.1 \pm 1.9^A$ | $14.2 \pm 0.6^{AB}$ | $17.3 \pm 1.5^A$ | $15.2 \pm 2.4^A$ | $17.4 \pm 2.3^A$ | $20.2 \pm 1.8^{AB}$ |
| GLU (mg/dl) | $216.1 \pm 13.2^A$ | $224.1 \pm 21.2^A$ | $228.1 \pm 17.5^A$ | $258.6 \pm 28.2^{AB}$ | $219.8 \pm 8.2^A$ | $290.8 \pm 53.5^B$ |
| CPK (U/l) | $129.3 \pm 21.7^{AB}$ | $109.1 \pm 11.3^A$ | $100.9 \pm 14.7^A$ | $114 \pm 21.9^A$ | $88.3 \pm 5.8^B$ | $129 \pm 15.3^{AB}$ |

*All data are expressed as means + SD and were compared with the ANOVA (n = 6).
Differences with p < 0.05 are considered statistically significant.

The results suggest that TP3 do not induce systemic toxic effects, even at the highest concentration tested (2 mg/mouse).

1.17 TP3 Enhanced the Survival of Mice Infected with MRSA

Figure 2A:
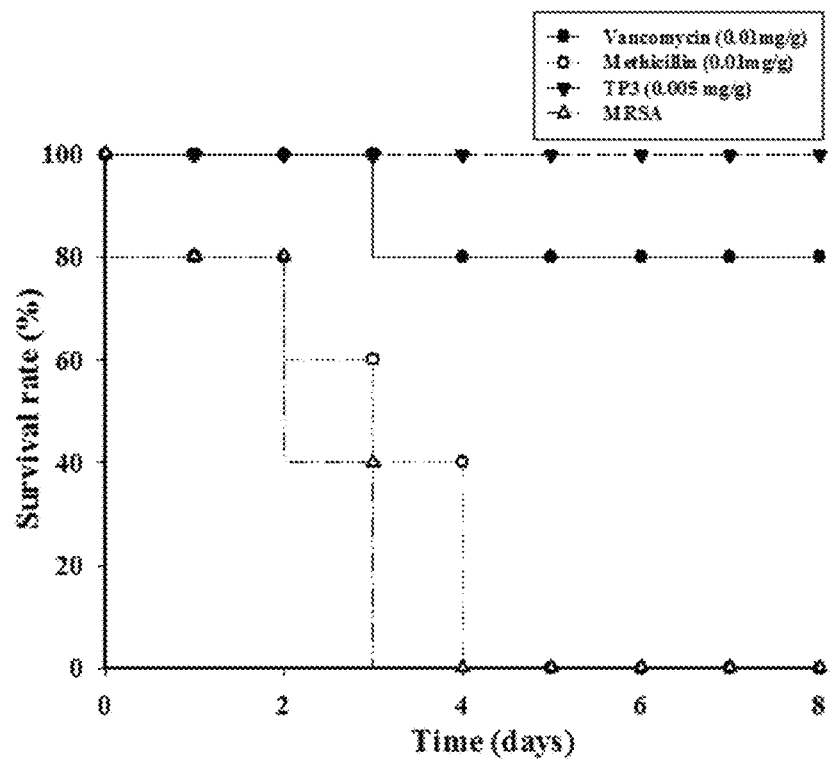
FIGS. 2A and 3B show the effects of the TP3-treatment on mice infected with MRSA.

The in vivo bactericidal effects of TP3 were investigated by monitoring the survival of mice infected with MRSA prior to treatment with TP3 or antibiotic. All untreated mice infected with MRSA died within 72 h of infection, whereas co-treatment with TP3 decreased the mortality rate, see FIG. 2A. At 8 days after MRSA infection, the survival rates were 100%, 80%, and 0% for mice treated with TP3 (0.005 mg/g), vancomycin (0.01 mg/g), and methicillin (0.01 mg/g), respectively. The rates of lethality by 48 h in the untreated groups were 20% in mice infected with MRSA, and treatment with TP3 or vancomycin significantly decreased the rate of mortality (Table 2). Bacteriologic evaluation revealed that untreated mice infected with either strain exhibited 100% positive blood cultures and a high level of bacterial colonization (with the numbers of CFU/g being no lower than $10^6$) for all organs tested (Table 2).

pected, as skin wounds heal efficiently in healthy mice, and it is unlikely that this process could be significantly improved. However, untreated infected wounds resulted in death in the first week, see FIG. 3B. Treatment with vancomycin resulted in a similar wound closure time to the control, while wound closure was accelerated by treatment with TP3 alone. Such an increase in wound closure was not observed in uncontaminated wounds, suggesting that TP3 facilitate wound recovery by combating infection. Unlike the uncontaminated wounds, wound size was largely unchanged after one week in all treatment groups, see FIG. 3B. By 14 days, wound size in the TP3-treated group was smaller than that of the vancomycin-treated group (P<0.05).

1.19 Microbial Loads in Treated Wounds

The increase in wound size in untreated contaminated wounds, and the lack of closure in the MRSA and MRSA+ Meth (methicillin) treatment groups (FIG. 3B) suggested active wound infection. This was supported by quantitative assessment of the wound flora (Table 3).

TABLE 2

Effect of TP3, methicillin and vancomycin on mice survival following intraperitoneal injection of $1 \times 10^6$ CFU of MRSA each mouse.

| Strain and Treatment | % lethality | Mean ± SD count (CFU/ml) | | | | |
|---|---|---|---|---|---|---|
| | | Blood | Peritoneum | Spleen | Liver | Mesenteric lymph nodes |
| MRSA | | | | | | |
| MRSA + PBS | $20^B$ | $5.8 \times 10^7 \pm 1.4 \times 10^{7B}$ | $1 \times 10^{10} \pm 3.6 \times 10^{9B}$ | $6.8 \times 10^8 \pm 3 \times 10^{8B}$ | $2.1 \times 10^8 \pm 9.2 \times 10^{7B}$ | $5.4 \times 10^7 \pm 2.6 \times 10^{7B}$ |
| MRSA + Methcillin (0.01 mg/g) | $20^B$ | $5.8 \times 10^7 \pm 1.7 \times 10^{7B}$ | $4.9 \times 10^9 \pm 2.2 \times 10^{9B}$ | $9.5 \times 10^8 \pm 1.9 \times 10^{8B}$ | $3.7 \times 10^8 \pm 8.1 \times 10^{7B}$ | $6.4 \times 10^7 \pm 5.3 \times 10^{7B}$ |
| MRSA + Vancomycin (0.01 mg/g) | $0^A$ | $8 \times 10^3 \pm 1.3 \times 10^{5B}$ | $2.7 \times 10^9 \pm 1.5 \times 10^{9A}$ | $1.8 \times 10^3 \pm 8.4 \times 10^{7B}$ | $1.7 \times 10^8 \pm 3.8 \times 10^{7B}$ | $2 \times 10^8 \pm 4.4 \times 10^{6A}$ |
| MRSA + TP3 (0.005 mg/g) | $0^A$ | $0^A$ | $1.4 \times 10^9 \pm 1 \times 10^{9A}$ | $9 \times 10^7 \pm 8.2 \times 10^{7A}$ | $4.4 \times 10^7 \pm 1 \times 10^{7A}$ | $1.6 \times 10^6 \pm 1 \times 10^{6A}$ |

*Lethality was monitored for 2 day following the injection of TP3 or antibiotic.

Figure 2B:
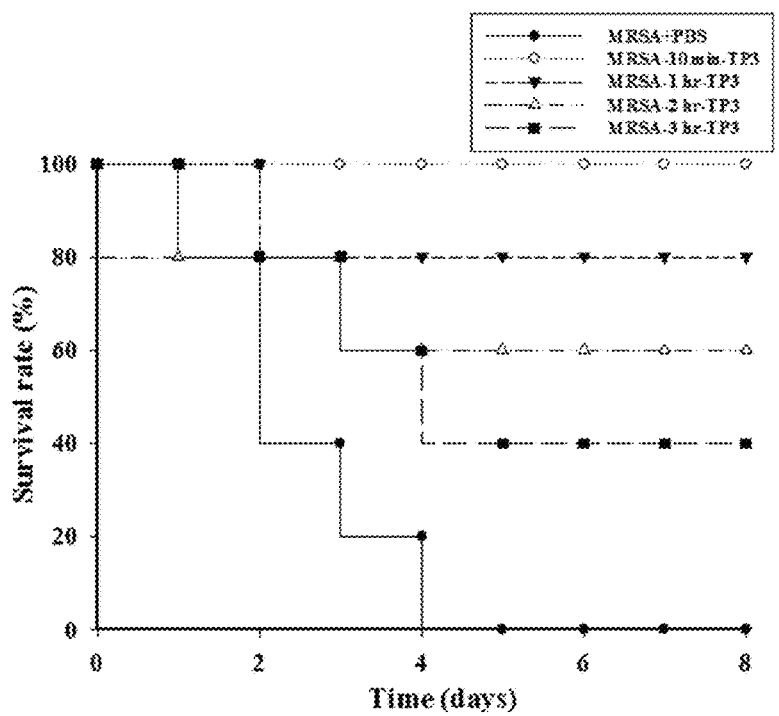
FIG. 2B shows the curative potential of TP3, wherein the mice were first injected with MRSA ($1 \times 10^6$ cfu/mouse) and then with TP3 (0.005 mg/g) 10, 60, 120, or 180 min later. At these injection times, the MRSA experimental groups exhibited survival rates of 100%, 80%, 60%, and 40%, respectively.

TP3 treatment significantly reduced the bacterial burden in all examined organs compared to that for the untreated controls (P<0.05). These data indicate that TP3 can efficiently control the MRSA in the organs of infected mice. To determine the curative potential, mice were first injected with MRSA and then injected with TP3 (0.005 mg/g) 10, 60, 120, or 180 min later. At these injection times, the MRSA experimental groups exhibited survival rates of 100%, 80%, 60%, and 40%, respectively, see FIG. 2B. The survival rates of mice treated with TP3 were consistently greater than those of untreated mice (PBS-treated control mice). These data indicate that immediate application of TP3 (0.005 mg/g) is important to prevent severe infection. Application within 10 to 60 min of MRSA infection enabled TP3 to act as an effective curative agent. TP3 was used for tests of wound healing infection experiments and explored antibacterial activity and promote wound repair.

1.18 Efficacy of TP3 on In Vivo Wound Closure

Figure 3A:
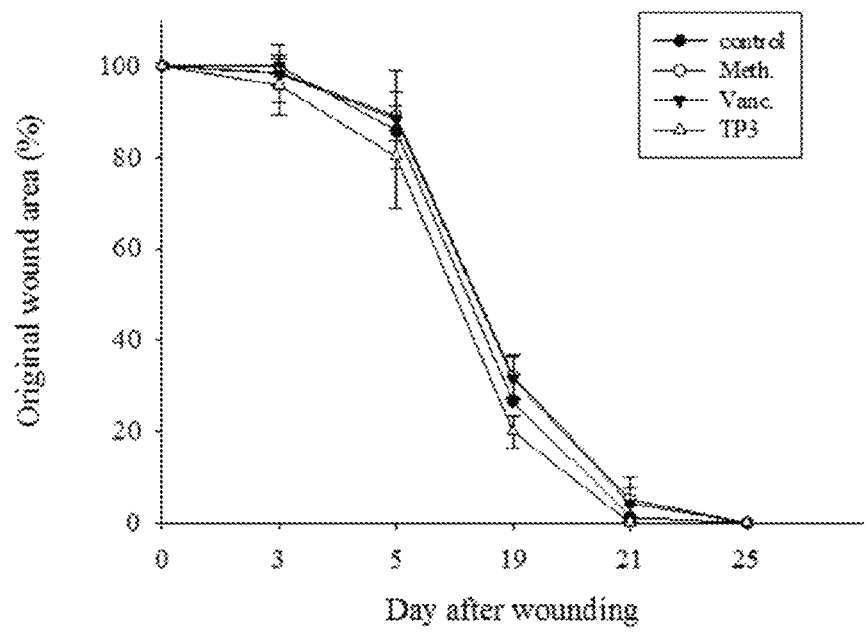
FIGS. 3A and 4B show the effects of closure of clean and contaminated wounds after the T3 treatment, wherein the areas of full-thickness wounds (initially 1 cm in diameter) were measured from the time of wounding until closure.
Figure 3B:
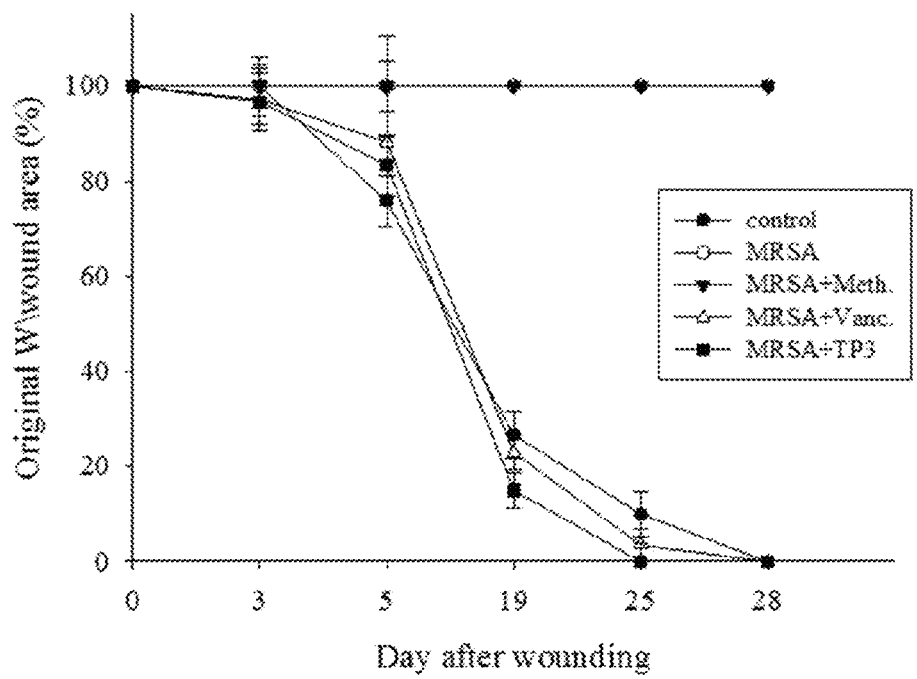

The effects of TP3 were determined in promotion of healing of wounds made in an aseptic manner, see FIG. 3A. No statistical difference was observed between the areas of untreated wounds and Tegaderm™ or antibiotic-treated wounds, with all closing by day >25. This was not unex-

TABLE 3

Bacterial load. Average of four mice at each time point; control refers to initial inoculation for each mouse.

| Organism | Condition | Day | Bacterial Count |
|---|---|---|---|
| MRSA | MRSA | 0 | $4.5 \times 10^4$ CFU/10 μl |
| | | 3 | $7.3 \times 10^7$ CFU/10 μl |
| | | 5 | Fatal |
| | MRSA + Meth. | 0 | $5.2 \times 10^4$ CFU/10 μl |
| | | 3 | $6.7 \times 10^7$ CFU/10 ml |
| | | 5 | Fatal |
| | MRSA + Vanc. | 0 | $4.9 \times 10^4$ CFU/10 μl |
| | | 3 | $3 \times 10^5$ CFU/10 μl |
| | | 5 | $2.6 \times 10^3$ CFU/10 μl |
| | | 19 | 42 CFU/10 μl |
| | MRSA + TP3 | 0 | $4.3 \times 10^4$ CFU/10 μl |
| | | 3 | $1 \times 10^4$ CFU/10 μl |
| | | 5 | $1.42 \times 10^2$ CFU/10 μl |
| | | 19 | 0 CFU/10 μl |

The initial inoculum of approximately $4.5 \sim 5.2 \times 10^4$ cfu/10 μl of each organism increased to about $6.7 \sim 7.3 \times 10^8$ cfu/10 μl in the MRSA and MRSA+Meth groups by day 3. Between days 3 and 5, the colony counts in the MRSA+Vanc and MRSA+TP3 groups decreased, with the most rapid decrease being observed in the TP3 group (significantly different as compared to the other groups at day 5). In clinical practice, attempts to count MRSA colonies through culturing anaerobes from skin wounds often result in underestimates, due to the aerobic nature of the site.

The wounds were evaluated using Gram staining of tissues, to determine if anaerobes on the skin exceeded the counts achieved by quantitation of aerobes. Quantitation of the number of Gram-positive organisms per high-power field in the upper dermis reflected the quantitative cell counts. As expected, bacterial loads were reduced more quickly upon treatment with antimicrobial agents.

1.20 Evaluation of Dermal and Epidermal Maturation

The above data demonstrating enhanced wound closure suggest that treatment with TP3 alone facilitate maturation of the dermal matrix. Dermal maturation is normally assessed at the proliferation, remodeling, and maturation stages. Wounds treated with TP3 exhibited accelerated progression at all three of these stages. Accelerated healing was also noted in the epidermal compartment.

Wounds treated with TP3 were multilayered as in normal skin, and fully mature by day 25. Keratinization and regeneration of the epithelium showed no signs of irregularity, whereas wounds treated with Tegaderm™ and MRSA+Vanc displayed impairment in overall epidermal maturation as compared to the TP3 group. As such, the effects of TP3 to promote the innate immune response and cytokine production were tested after the treatment in infected mice. Giemsa staining revealed accumulation of immune cells in the skin of infected mice treated with MRSA.

1.21 Mechanism of TP3 Activity

Figure 4A:
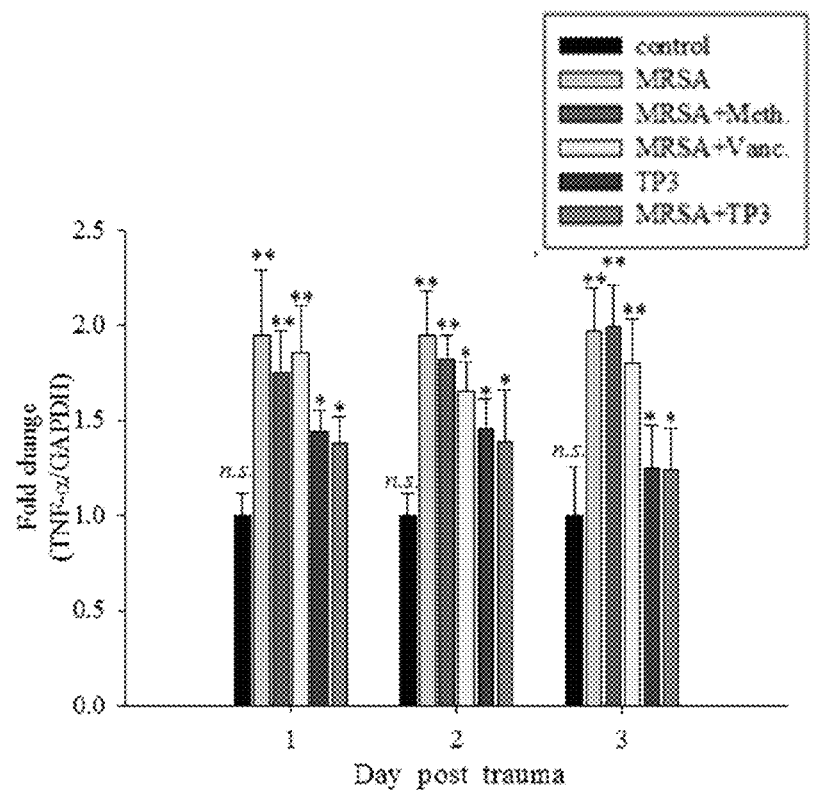
Figure 4B:
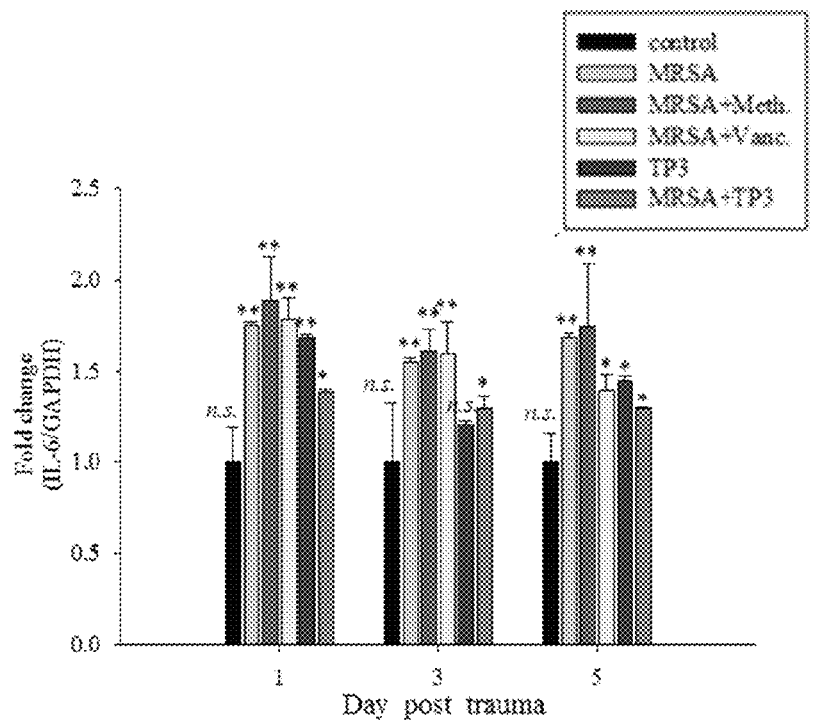
Figure 4C:
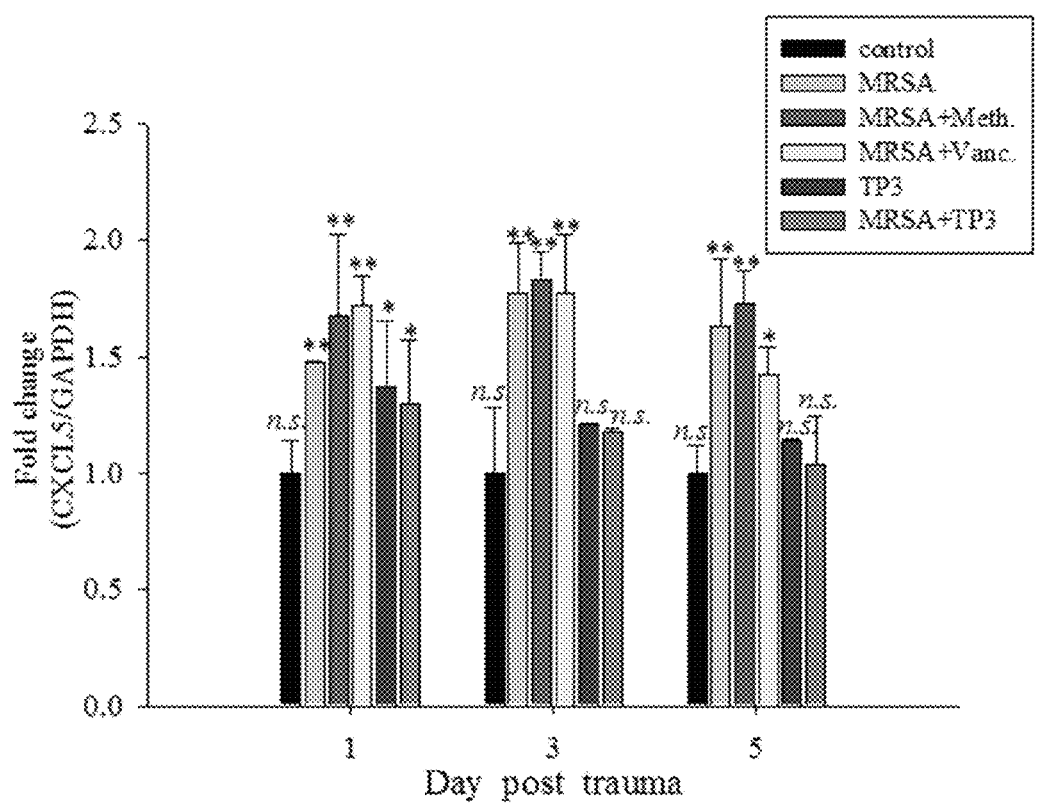

The mechanism underlying the direct antimicrobial activity of TP3 was examined. The ability of TP3 to modulate the immune cells of mice was measured using IHC and real-time PCR. IHC with cell surface marker antibodies revealed a significant increase in the infiltration of macrophages, lymphocytes, and CD8 (cytotoxic cells) in infected wounds treated antibiotic and less discovery in TP3 group. The reason may be as antimicrobial peptides directly kill bacteria, reduce the affected area of the mouse innate immune response. The pro-inflammatory cytokine IL-6 acts as a potent modulator of innate immunity, while the chemokine CXCL5 enhances the recruitment of macrophages to tissue surrounding wounds. Wound tissue chemokine and cytokine levels in MRSA-infected mice were measured at 1, 3 and 5 days after treatment. MRSA-infected mice were used as a positive control to confirm cytokine activation. TP3 treatment decreased induction of TNF-α, IL-6, and CXCL5 as compared to the positive controls (FIG. 4A-4C).

In summary, TP3 possessed antimicrobial activities in view that the wound closure activities of TP3 were confirmed both in vitro and in vivo. TP3 did not affect the viability of baby hamster kidney cell up to 40 μg/ml, and MICs of TP3 against MRSA were determined. TP3 was found to be highly effective at combating peritonitis and wound healing infection caused by MRSA in mouse models, without inducing adverse behavioral effects or liver or kidney toxicity. The results indicated that TP3 enhances the rate of survival of mice infected with the bacterial pathogen MRSA through both antimicrobial and immunomodulatory effects, suggesting that TP3 can be developed as a novel topical agent for wound healing, particularly MRSA infection in wounds.

Example 2 Efficacy Experiments for TP4

Materials and Methods 2.1. Bacteria, Cells, and Mice

An MRSA strain commonly associated with human wound infections was selected to generate a polymicrobial solution. The MRSA strain is a clinical isolate from stool obtained from Taipei City Hospital (Heping Fuyou branch). The strain was identified by routine laboratory methods and stored in 20% (vol/vol) glycerol at −80° C. Tryptic Soy Broth (TSB) was used as the culture medium. HaCaT human keratinocyte cell line and Hs-68 human foreskin fibroblast cell line were grown in DMEM containing 10% (v/v) FBS, 0.37% (w/v) $NaHCO_3$, penicillin (100 unit/ml), streptomycin (100 μg/ml), 0.1 mM NEAA, and 1 mM sodium pyruvate at 37° C. in a humidified incubator under 5% $CO_2$ and 95% air. The cells were harvested at ca. 90% confluence (ca. $10^6$ cells/10-cm dish). Balb/c female mice were used for the experiments. All mice were housed in cages under specific pathogen-free conditions, and given water and standard laboratory chow ad libitum during the experiments. All animal handing procedures were in accordance with National Taiwan Ocean University (NTOU) guidelines. All procedures were approved by the Animal Care and Use Committee of NTOU.

2.2 Peptides, Reagents, and Antibodies

Reagents and chemicals were purchased from Sigma (St. Louis, Mo.). Standard laboratory powders of methicillin (catalog no. 51454; Sigma, St. Louis, Mo.) and vancomycin (catalog no. v2002; Sigma, St. Louis, Mo.) were used and prepared according to the guidelines of the CLSI. Tilapia piscidin 4 (TP4) having a sequence of HFIHHIIGGLFSAG-KAIHRLIRRRRR-OH (SEQ ID No: 14) was synthesized by solid-phase peptide synthesis and purified by reverse-phase high-performance liquid chromatography to a grade of >98.19% by GL Biochemistry (catalog no. 080571; Shanghai, China). ELISA kits for Interleukin-1 (Cat no. 559603, BD Biosciences, CA, USA), tumor necrosis factor (Cat no. 560478, BD Biosciences, CA, USA), and Interleukin-6 (Cat no. 555240, BD Biosciences, CA, USA) were used to determine cytokine levels. Antibodies against VEGF (Cat no. 550549, BD Biosciences, CA, USA) were used for immunohistochemistry (IHC).

2.3 Cell Proliferation

Cells were cultured at a density of $5 \times 10^4$ cells per well in flat-bottomed 96-well plates. At subconfluence, the cells were incubated with various stimuli and concentrations of TP4 for 48 h. Cell proliferation was measured by neutral red, LDH, and MTT assay, according to the manufacturer's instructions. Cellular morphology was observed under microscopy (BX-51, Olympus, Japan).

2.4 Measurement of Collagen I, Collagen III, KGF, Keratin 10, and Keratin 17 Expression Total RNA was isolated from HaCaT and Hs-68 cells, and purified using a Qiagen RNeasy kit. Reverse transcription into cDNA was performed with an iScript cDNA Synthesis Kit (BIO-RAD, USA) according to the manufacturer's recommendations. Real-time polymerase chain reaction (PCR) was performed to analyze gene expression, using 0.5 ml of cDNA, 2× iQSYBR® Green Supermix (BIO-RAD, USA), and 500 nM of forward and reverse primers against selected genes or GAPDH (reference gene), according to the instructions of the manufacturer. Quantitative PCR was performed under the following conditions: 40 cycles of 1 min at 95° C., 30 s at 55° C., and 1 min at 72° C. The threshold cycle number (Ct) was calculated with BIO-RAD software. Relative transcript quantities were calculated using the ΔCt method with GAPDH as the internal reference gene. ΔCt is the difference in the threshold cycles of messenger (m)RNA for selected genes relative to those of GAPDH mRNA. Real-time PCR was performed in triplicate for each experimental group.

Primer sequences:

GAPDH (Nm_002046)
F-
CGCTCTCTGCTCCTCCTGTTC (SEQ ID No: 24)

R-
TTGACTCCGACCTTCACCTTCC (SEQ ID No: 25)

Collagen I (NM_000088)
F-
ACAGGGCGACAGAGGCATAAAG (SEQ ID No: 26)

R-
CCAGGAGCACCAGCAGAGC (SEQ ID No: 27)

Collagen III (NM_000090)
F-
TCCAAAGGGTGACAAGGGTGAAC (SEQ ID No: 28)

R-
AGGAGGACCAATAGGACCAGTAGG (SEQ ID No: 29)

KGF (S81661)
F-
GCAACTGAACTTACTACGAACTG (SEQ ID No: 30)

R-
TCATTGACCTCTTCCTATCTGTG (SEQ ID No: 31)

Keratin 10 (AF264085)
F-
CTGCGTAGGGTGCTGGATGAG (SEQ ID No: 32)

R-
TTCCTCCTCGTGGTTCTTCTTCAG (SEQ ID No: 33)

Keratin 17 (NM_000422)
F-
CTGGCTGCTGATGACTTCC (SEQ ID No: 34)

R-
CCTCCTCGTGGTTCTTCTTC (SEQ ID No: 35)

2.5 Tilapia Piscidin 4 Peptides and Bacteriostatic Analysis

Minimum inhibitory concentration (MIC) antimicrobial assays were performed using standard protocols. For MIC assessment, compounds were diluted to final concentrations of 100, 50, 25, 12.5, 6.25, 3.125, 1.582, or 0.78 g/ml. Twenty microliters of each dilution were mixed in a microtiter plate well with 20 μl of the appropriate bacterial indicator suspension, and 160 μl of Trypticase Soy Broth (TSB) for $S.$ $aureus$, to a total volume of 200 μl. Three replicates were examined for each $S.$ $aureus$ strain, compound, and concentration. Positive controls contained water instead of compounds, and negative controls contained compounds without bacterial suspensions. Microbial growth was automatically determined by optical density measurement at 600 nm (Bioscreen C, Labsystem, Helsinki, Finland). Microplates were incubated at 25° C. for plant pathogens and at 37° C. for food-borne bacterial strains. Absorbance readings were taken at hourly intervals over a 48 h period. Plates were shaken for 20 s before each measurement. The experiment was repeated twice. The lowest compound concentration that resulted in zero growth by the end of the experiment was taken as the MIC.

2.6 In Vivo Toxicity

To determine the toxicity of TP4, TP4 was dissolved in phosphate-buffered saline (PBS; pH 7.4) and administered as intramuscular bolus injections in the left thigh (2 mg/mouse). Each group contained 10 mice. Controls were treated with PBS (control). Blood samples (0.2 ml) were collected on days 1, 3, and 6 after the final injection of TP4, and used to determine the serum levels of glutamic oxaloacetic transaminase (GOT), glutamic pyruvic transaminase (GPT), blood urea nitrogen (BUN), creatinine (CRE), total glucose (GLU), and creatine phosphokinase (CPK).

2.7 Therapeutic Use in a Mouse Model of MRSA Sepsis

Female Balb/c mice (6-8 weeks old) were injected intraperitoneally with $10^6$ CFU MRSA per mouse. Ten minutes after MRSA injection, mice were injected intraperitoneally with vancomycin (0.01 mg/g mouse body weight), methicillin (0.01 mg/g mouse body weight), or TP4 (0.005 mg/g mouse body weight). In a second set of experiments, mice were given intraperitoneal injections of TP4 (0.005 mg/g mouse body weight) at 10, 60, 120, or 180 min after MRSA injection. Survival rate and status were recorded every 24 h for up to 192 h. To examine bacterial dissemination, mice were sacrificed at 48 h after injection with antibiotics or TP4, and the bacterial numbers in blood, peritoneum, spleen, liver, and mesenteric lymph nodes were recorded. Colony counts from the diluted bacterial solutions were expressed relative to those at the start of treatment. These experiments consisted of four groups, and each group contained 10 mice.

2.8 Mouse Models of Wound Healing

Female Balb/c mice (6-8 weeks old) were used for wound healing experiments. All mice were housed individually to prevent fighting and further damage to the wounds, and they were provided with food and water ad libitum. Mice were maintained on a 12 h light: dark cycle at room temperature, and acclimatized to the environment for at least a week before use in experiments. All researchers wore caps, sterile gloves, gowns, and shoe covers when handling mice. Hair was removed from the back of the mice by shaving, and a full thickness wound (1 cm in diameter) was then created in the exposed region. Each wound was inoculated with 50 μl of broth mix containing $10^6$ cfu (colony forming units) of $S.$ $aureus$. At 5 min after inoculation, 50 μl TP4 (2 mg/ml) in a total volume of 0.1 ml were applied. Thirty minutes after treatment, wounds were covered with Tegaderm (3M, St. Paul, Minn.) to maintain uniformity, and to prevent the mice from removing the treatments. Based on initial experiments, we examined the wounds at 3, 7, 14, and 21 days post-injury, so as not to disturb the infection. Such examinations captured the transitions from inflammatory to regenerative, and regenerative to resolving phases of wound healing. Animals were subsequently euthanized by $CO_2$ inhalation and the wounds assessed. Four individuals in each group were examined at each time point for each experiment. Each wound was measured and then removed from the animal, with unwounded skin taken from the contralateral dorsum as a control. Each biopsy was divided into six sections, with three sections being used for tensiometry and histology, and three sections for quantitative determination of microbial load. Wound healing studies were repeated in triplicate.

2.9 Wound Closure Measurements and Cell Proliferation Gene Expression

Tracings were taken immediately after injury. For uncontaminated wounds, wound size was determined every second day. For contaminated wounds, mice were euthanized at days 3, 5, or 19, and tracings of the wound edges were made. Wound areas were determined using the Macintosh Adobe Photoshop program, Histogram Analysis. The percentage of wound contraction was calculated as follows: % Wound contraction=(A0−At)/A0×100, where A0 is the original wound area, and at is the area of wound at the time of biopsy, accordingly. Cell proliferation gene expression was performed by real-time PCR, using the methods described above.

```
                  Primer sequences:

GAPDH (GU214026.1)
         F-
                                        (SEQ ID No: 36)
         CTCCAAGGAGTAAGAAACCC

R-
                                        (SEQ ID No: 37)
         TGGAAATTGTGAGGGAGATG

EGF (AF125256.1)
         F-
                                        (SEQ ID No: 38)
         CATATGTGATGGCTACTGCT

R-
                                        (SEQ ID No: 39)
         TTAATGTTCCTCAGGGAAGC

TGF-b (M57639)
         F-
                                        (SEQ ID No: 40)
         CGTGCTCTTCTTCGACAATA

R-
                                        (SEQ ID No: 41)
         AACATGAACAAACAGTCCCT

VEGF (AB086118.1)
         F-
                                        (SEQ ID No: 42)
         ACCTTTGGGAAGAAGATGTC

R-
                                        (SEQ ID No: 43)
         CAATAGAACCCTCGAGTGAG
```

2.10 IHC and ELISA of Cytokines

Skin tissues were removed and fixed as previously described. In brief, the cryosections were fixed with 4% formaldehyde, and the tissue samples were stained with VEGF. IHC was analyzed by three independent investigators. Images were taken using a BX-51 microscope (Olympus, Japan). ELISA was performed as previously described.

2.11 Statistical Analysis

All experiments were performed in triplicate on three biological replicates. Error bars represent the standard deviation, and significant differences between groups (P<0.05) were determined using analysis of variance (ANOVA). Different letters above the bars were used to indicate significant differences between groups. Groups of mice were used for each treatment, and each experiment was repeated three times.

Results 2.12 In Vitro Toxicity and Stimulation of Proliferation by TP4

Figure 5A:
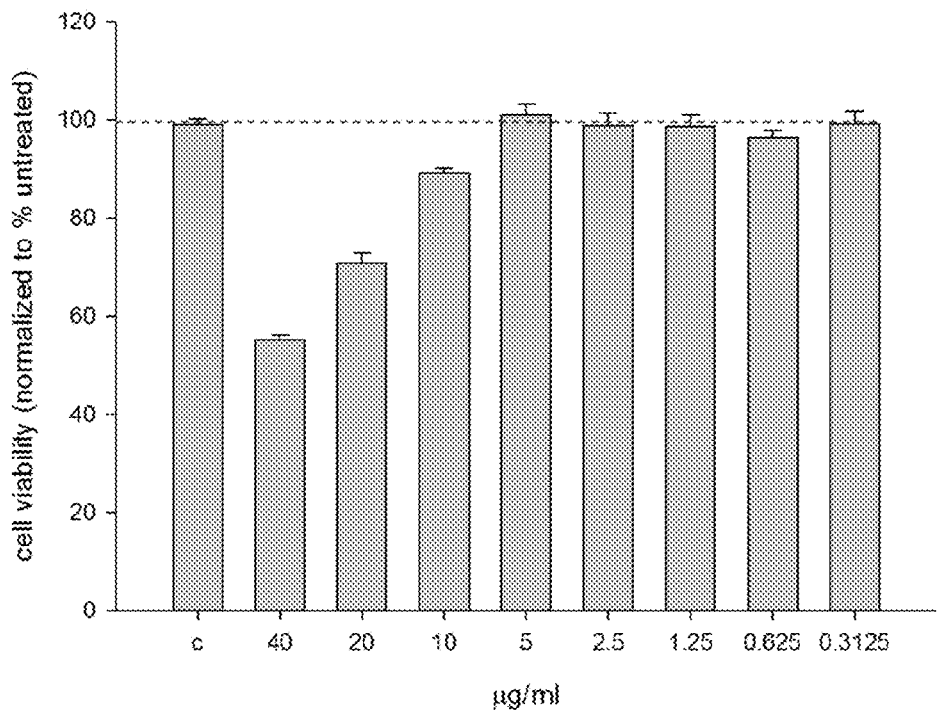
FIG. 5A-5F show that TP4 did not exhibit cytotoxic effects on a human fibroblast cell line (Hs-68), and actually stimulates proliferation activity.
Figure 5B:
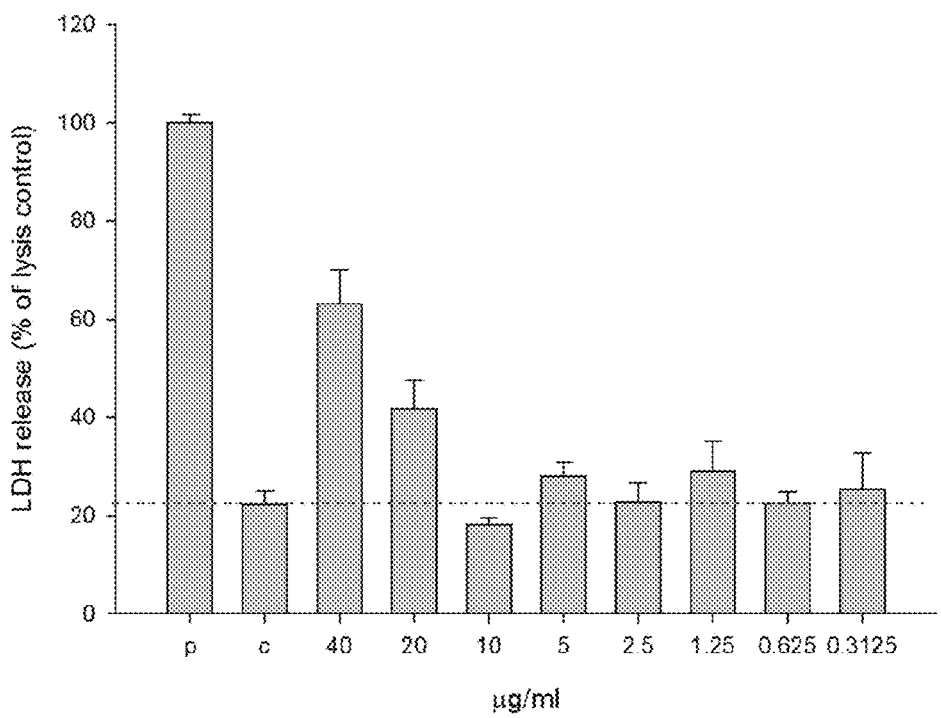
Figure 5C:
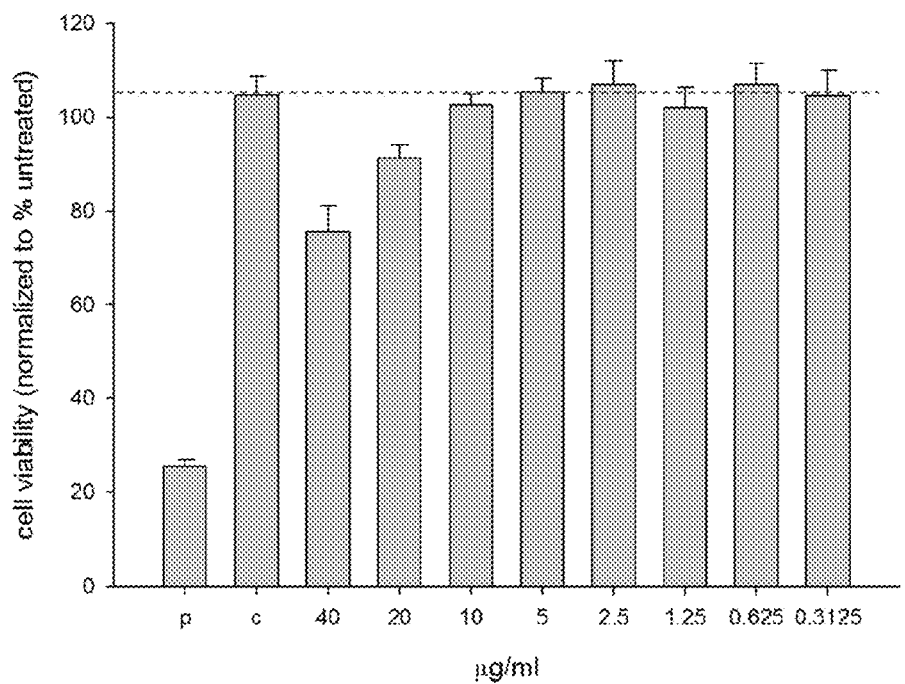
Figure 5D:
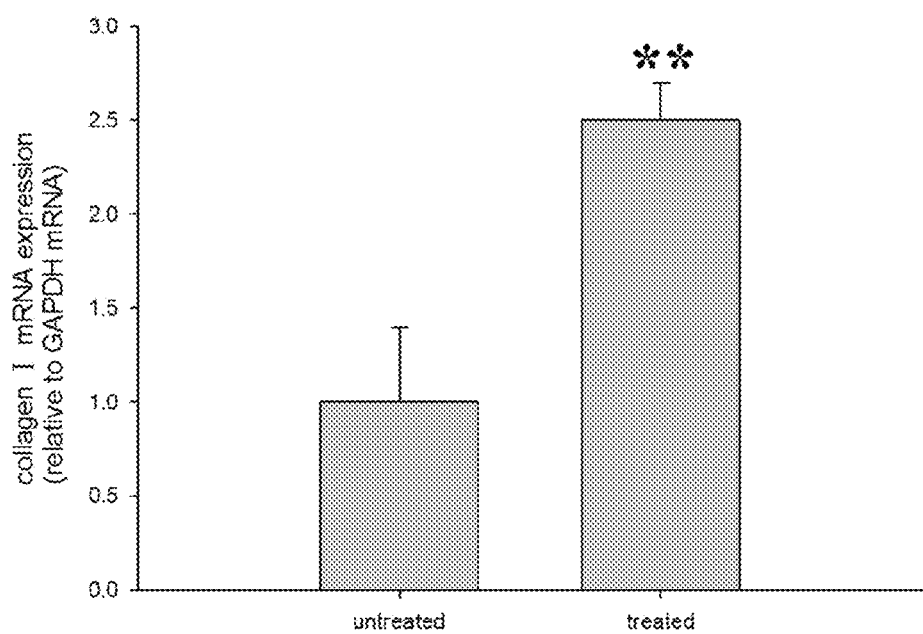
Figure 5E:
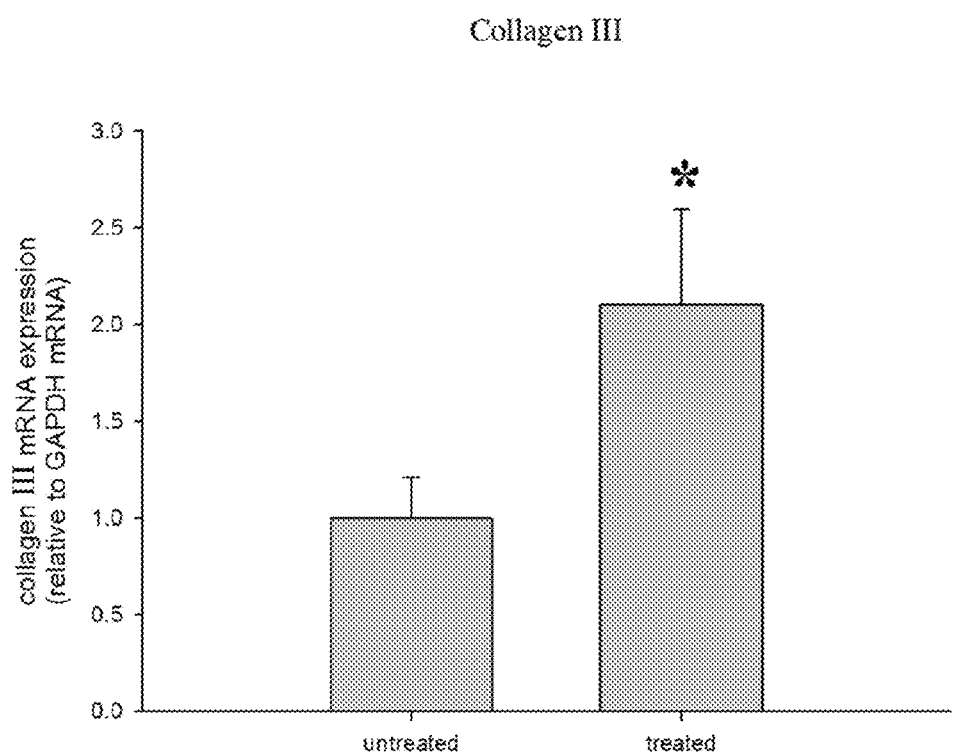
Figure 5F:
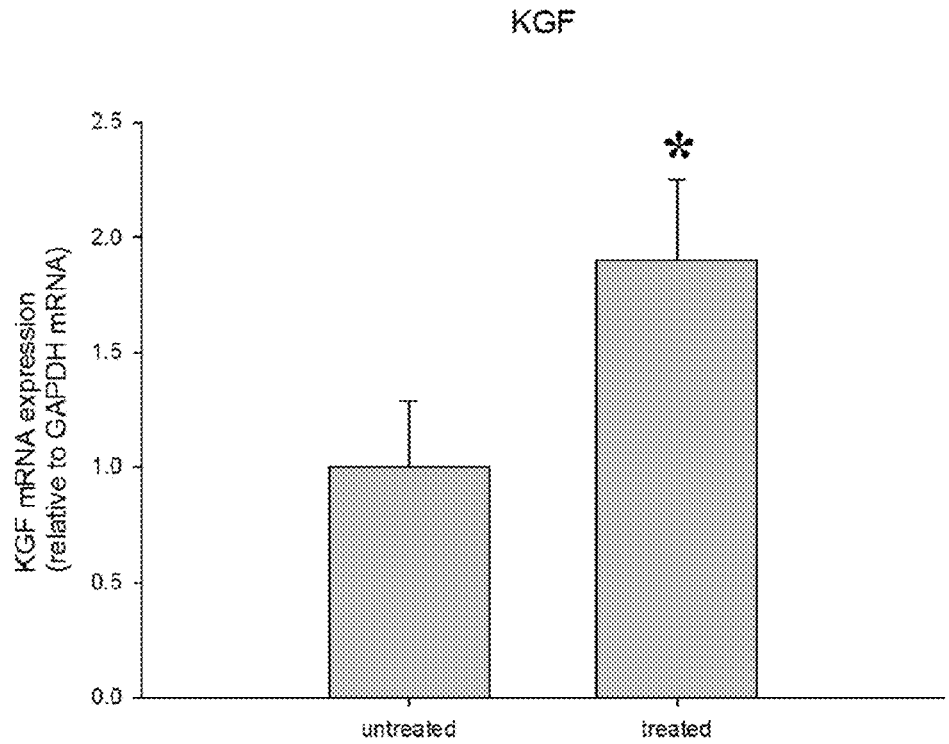

The cell toxicity of TP4 in a fibroblast cell line (Hs-68) and a keratinocyte cell line (HaCaT) was tested using neutral red, LDH, and MTT assays; it was observed that TP4 at Hs-68 line, see FIG. 5A-5C. In addition, cell proliferation was significantly increased by low doses (2.5~10 n cell viability as compared to the untreated group. TP4 treatment also enhanced the amount of cell aggregates, in the form of ripple-like areas adhered to the surface. Subsequently, the effect of TP4 on cell proliferation factors was investigated. Collagen and keratinocyte growth factor (KGF) are important performance factors for cell proliferation. Collagen I and III, and KGF gene expression were analyzed in TP4 treated Hs-68 cells. Expression of all genes was enhanced by TP4 treatment, as compared to expression in the controls, see FIG. 5D-5F.

Figure 6A:
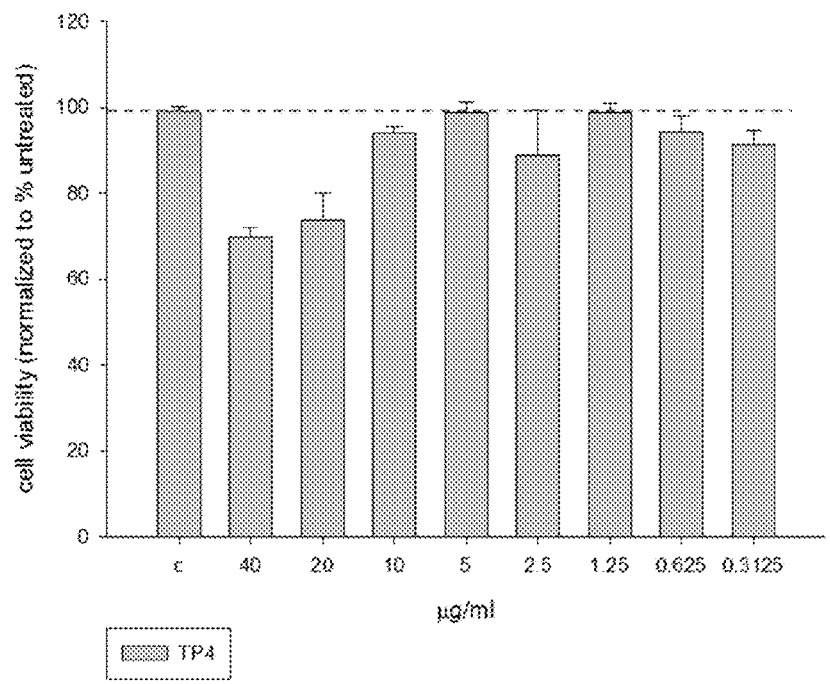
FIG. 6A-6E show that TP4 did not exhibit cytotoxic effects on a human keratinocyte cell line (HaCaT), and actually stimulates proliferation activity.
Figure 6B:
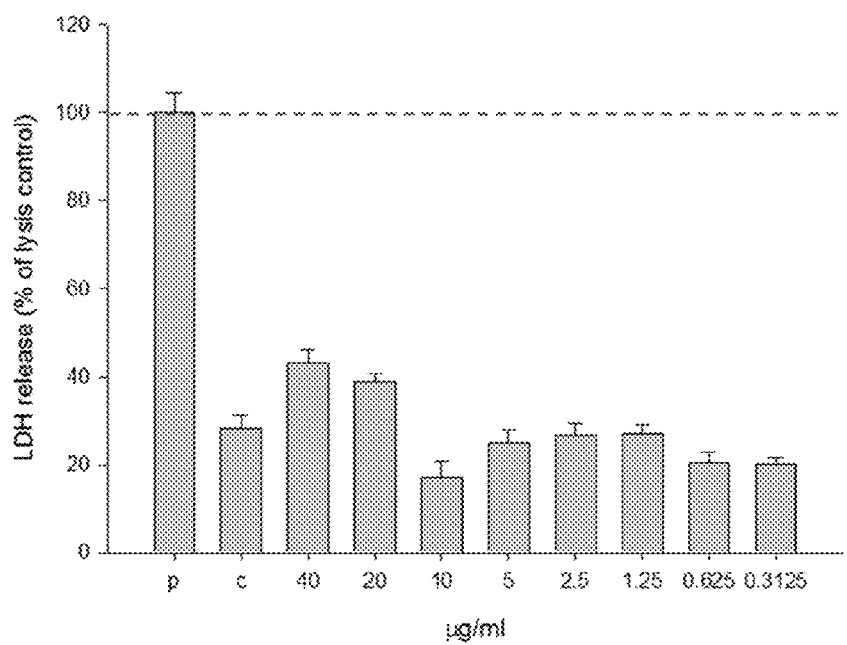
Figure 6C:
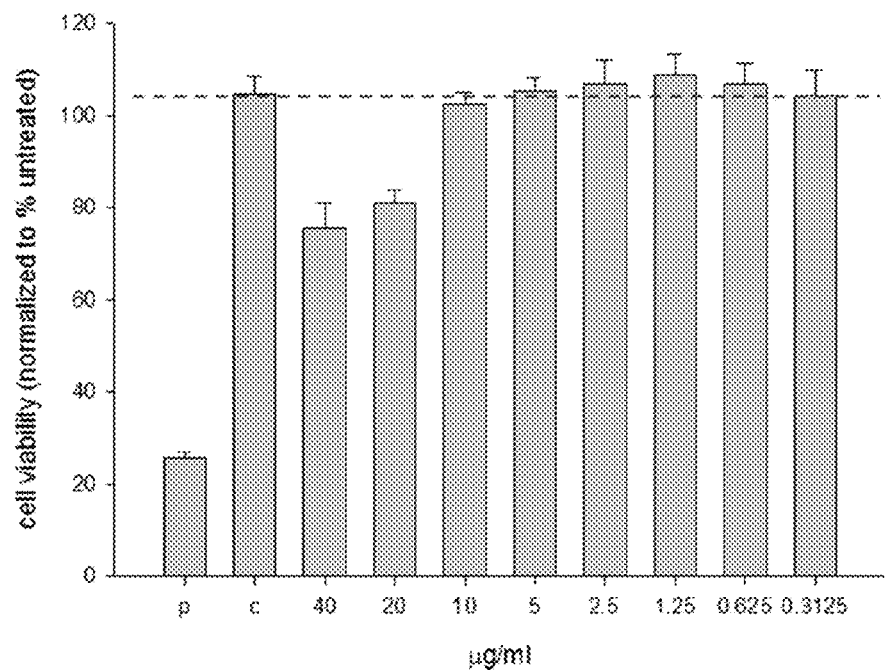
Figure 6D:
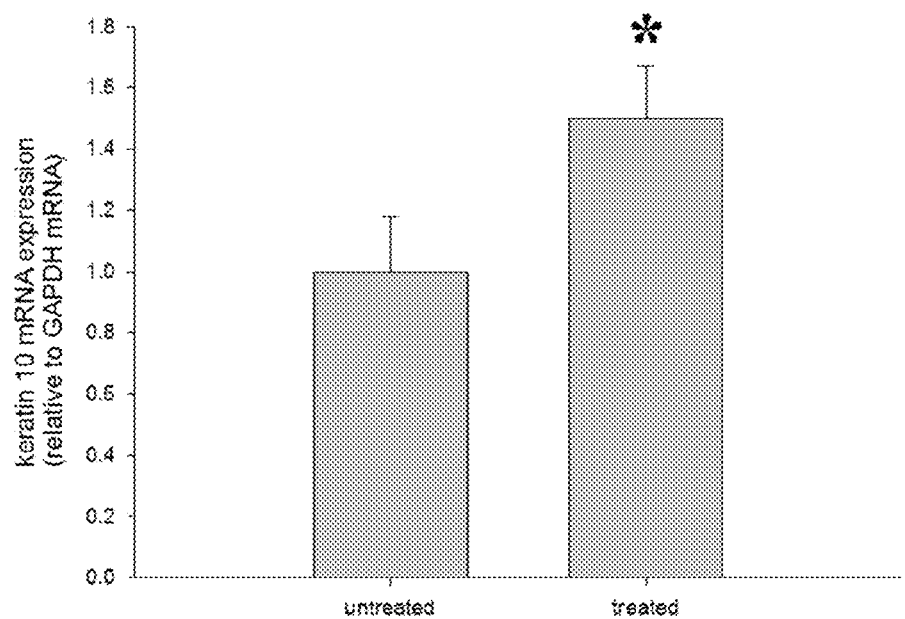
Figure 6E:
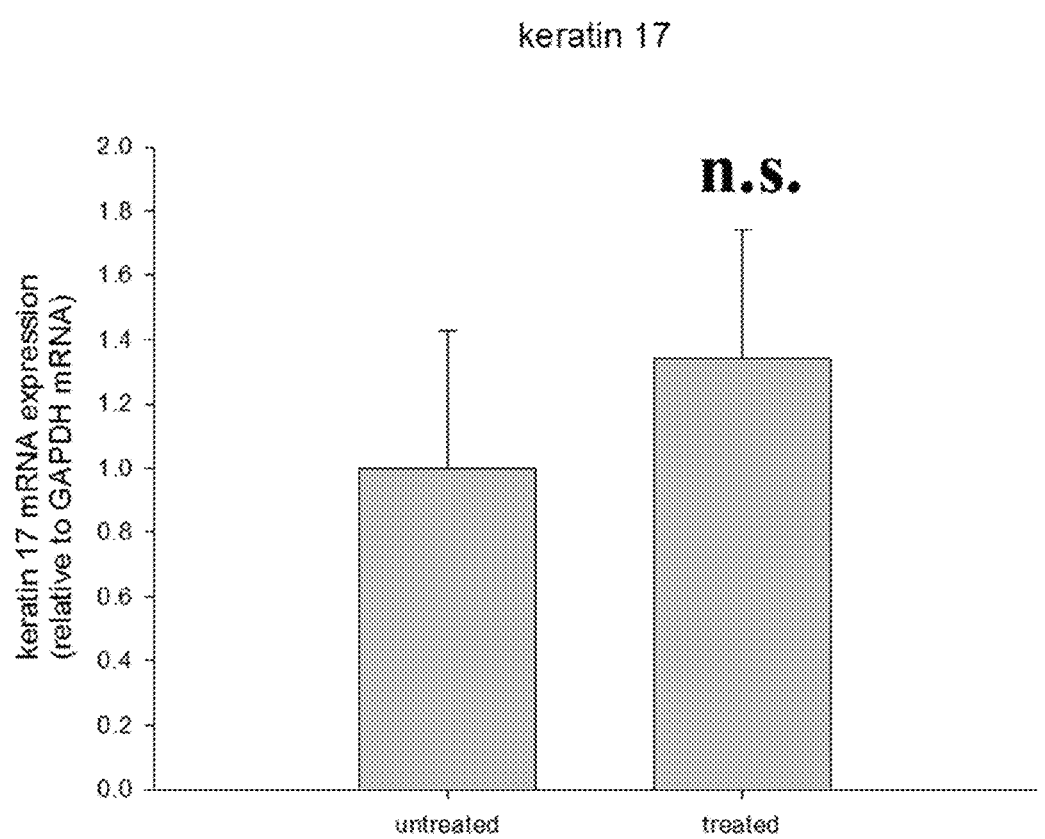

Similar results were also observed for TP4-treated HaCaT cells. TP4 at tested concentrations (down to 10 µg/ml) did not affect viability of HaCaT cells, see FIG. 6A-6C. Of the proliferation and differentiation mediators in this keratinocyte cell line (HaCaT), keratin 10 and 17 are of particular importance, because they play a major role in coordinating protein synthesis and cell growth mechanisms. As shown in FIG. 6D, TP4 significantly increased gene expression of keratin 10, but did not affect that of keratin 17, see FIG. 6E. Therefore, the results indicated that TP4 enhanced Hs-68 and HaCaT cell proliferation, possibly through activation of the genes encoding collagen I and III, KGF, and keratin 2.13 Acute Toxic Effects of TP4 in Mice The toxicity of TP4 was examined by delivering it via intramuscular (i.m.) injection into mice, and subsequently measuring biochemical factors in the blood. Mice treated with 2 mg of TP3 did not exhibit any significant changes in the levels of glutamic oxaloacetic transaminase (GOT), glutamic pyruvic transaminase (GPT), blood urea nitrogen (BUN), creatinine (CRE), total glucose (GLU), or creatine phosphokinase (CPK) (Table 4). Our results suggest that TP4 does not induce systemic toxic effects, even at the highest concentration tested (2 mg/mouse).

TABLE 4

Biochemical parameters of mice after intramuscular injection of TP4 (2 mg/mouse).

| | Control (n = 10) | | | TP4 (n = 10) | | |
|---|---|---|---|---|---|---|
| Time (Day) | 1 | 3 | 6 | 1 | 3 | 6 |
| GOT (U/L) | 42.1 ± 1.3$^A$ | 44.2 ± 2.1$^A$ | 41.6 ± 1.5$^A$ | 102.1 ± 32.1$^C$ | 43.2 ± 1.5$^A$ | 45 ± 6.1$^A$ |
| GPT (U/L) | 45.2 ± 1.1$^A$ | 43.4 ± 4.3$^A$ | 46.1 ± 3.3$^A$ | 81.2 ± 5.2$^C$ | 41.2 ± 4.7$^A$ | 48 ± 3.7$^A$ |

TABLE 4-continued

Biochemical parameters of mice after intramuscular injection of TP4 (2 mg/mouse).

| | Control (n = 10) | | | TP4 (n = 10) | | |
|---|---|---|---|---|---|---|
| Time (Day) | 1 | 3 | 6 | 1 | 3 | 6 |
| CRE (mg/dL) | $0.2 \pm 0.1^A$ | $0.6 \pm 0.3^A$ | $0.4 \pm 0.2^A$ | $0.3 \pm 0.1^A$ | $0.5 \pm 0.1^A$ | $0.5 \pm 0.1^A$ |
| BUN (mg/dL) | $13.1 \pm 2.1^A$ | $14 \pm 0.3^{AB}$ | $16.1 \pm 1^A$ | $14.2 \pm 1.4^A$ | $15.4 \pm 1.3^A$ | $16.2 \pm 1^A$ |
| GLU (mg/dL) | $206 \pm 11.1^A$ | $213.1 \pm 11.3^A$ | $208 \pm 13.1^A$ | $238.6 \pm 32.1^{AB}$ | $209.1 \pm 7.2^A$ | $220.1 \pm 23.5^A$ |
| CPK (U/L) | $101.3 \pm 1.7^A$ | $110.1 \pm 6.3^A$ | $104.9 \pm 4.2^A$ | $109 \pm 11.1^A$ | $108.1 \pm 3.2^A$ | $109 \pm 25.3^{AB}$ |

*All data are expressed as means + SD and were compared with the ANOVA (n = 10). The following parameters were measured in the blood: glutamic oxaloacetic transaminase (GOT), glutamic pyruvic transaminase (GPT), creatinine (CRE), blood urea nitrogen (BUN), and creatine phosphokinase (CPK). Each bar represents the mean value from three determinations ± standard deviation (SD). Data with different numbers differ significantly (P < 0.05).

2.14 TP4 Enhances the Survival of Mice Infected with MRSA

Figure 7A:
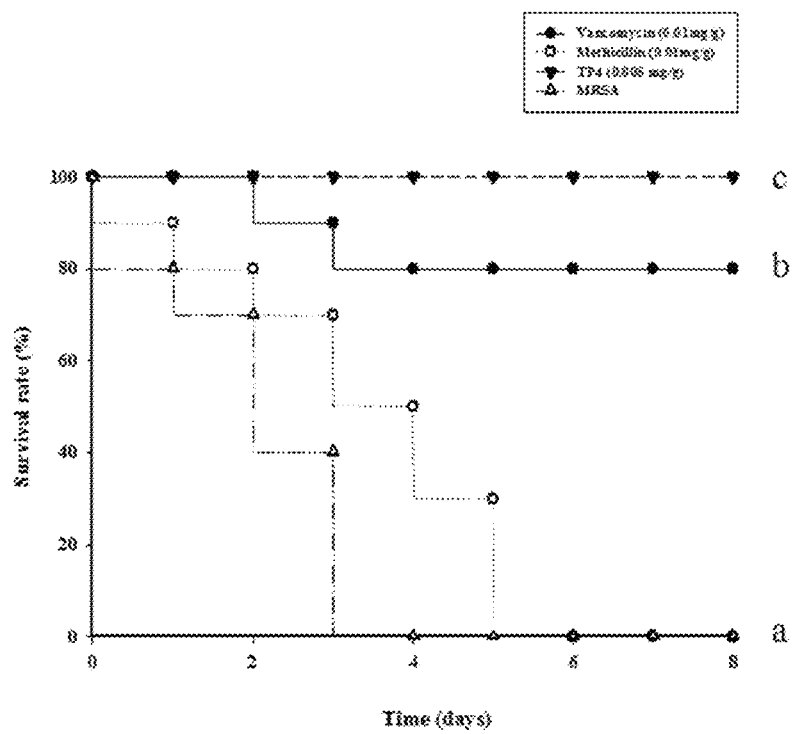
FIGS. 7A and 7B show the effects of the TP4-treatment on mice infected with MRSA.

The bactericidal effects of TP4 in vivo were evaluated by monitoring the survival of mice infected with MRSA prior to treatment with TP4 or antibiotic. All untreated mice infected with MRSA died within 72 h of infection, whereas co-treatment with TP4 decreased the mortality rate, see FIG. 7A. At 8 days after MRSA infection, the survival rates were 100%, 80%, and 0% for mice treated with TP4 (0.005 mg/g), vancomycin (0.01 mg/g), and methicillin (0.01 mg/g), respectively. At 48 h, the rate of lethality in the untreated and infected mice was 60%; treatment with TP4 or vancomycin significantly decreased the rate of mortality (Table 5). Bacteriologic evaluation revealed that untreated mice infected Application within 10 to 60 min of MRSA infection enabled TP4 to act as an effective curative agent. As such, the effects of TP4 were evaluated to promote wound repair.

As shown in Table 5, the bacterial counts at 48 hours after the last treatment in the indicated organs of mice infected with MRSA. Infected mice were untreated, or treated with TP4, methicillin, or vancomycin via i.p. injection. Bacterial numbers in blood, peritoneum, spleen, liver, and mesenteric lymph nodes were subsequently recorded. Colony counts from the diluted bacterial solutions are expressed relative to those at the start of treatment. Each value represents the mean value from three determinations±standard deviation (SD). Data with different numbers differ significantly (P<0.05).

TABLE 5

Bacterial counts at 48 hours after the last treatment in the indicted organs of mice infected with MRSA

| | | Mean ± SD count (CFU/mL) | | | | |
|---|---|---|---|---|---|---|
| Strain and Treatment | % lethality | Blood | Peritoneum | Spleen | Liver | Mesenteric lymph nodes |
| | | | MRSA | | | |
| MRSA + PBS | $60^C$ | $6 \times 10^8 \pm 1.9 \times 10^{7C}$ | $2.0 \times 10^{10} \pm 1.6 \times 10^{9C}$ | $5.9 \times 10^9 \pm 2 \times 10^{8C}$ | $2.1 \times 10^8 \pm 9.2 \times 10^{7C}$ | $3.2 \times 10^8 \pm 1.3 \times 10^{7C}$ |
| MRSA + Methcillin (0.01 mg/g) | $20^B$ | $4.1 \times 10^7 \pm 1.3 \times 10^{7B}$ | $2.3 \times 10^9 \pm 2 \times 10^{9B}$ | $1.5 \times 10^8 \pm 2.1 \times 10^{7B}$ | $2.7 \times 10^8 \pm 3.3 \times 10^{8B}$ | $4.1 \times 10^7 \pm 3 \times 10^{7C}$ |
| MRSA + Vancomycin (0.01 mg/g) | $10^{AB}$ | $8 \times 10^4 \pm 1.1 \times 10^{4B}$ | $1.5 \times 10^6 \pm 1 \times 10^{3A}$ | $1.4 \times 10^7 \pm 1.1 \times 10^{4B}$ | $1.3 \times 10^7 \pm 1.8 \times 10^{3B}$ | $1 \times 10^7 \pm 4 \times 10^{4B}$ |
| MRSA + TP4 (0.005 mg/g) | $0^A$ | $0^A$ | $1 \times 10^6 \pm 1 \times 10^{4A}$ | $3 \times 10^6 \pm 1.2 \times 10^{6A}$ | $2.4 \times 10^4 \pm 1 \times 10^{6A}$ | $6 \times 10^5 \pm 1 \times 10^{5A}$ |

*Lethality was monitored for 2 day following the injection of TP4 or antibiotic.

with either strain exhibited 100% positive blood cultures and a high level of bacterial colonization (with the numbers of CFU/ml being no lower than $10^6$) for all organs tested (Table 5). TP4 treatment significantly reduced the bacterial burden in all examined organs compared to those of untreated controls (P<0.05). These data indicate that TP4 can efficiently control MRSA in the organs of infected mice.

Figure 7B:
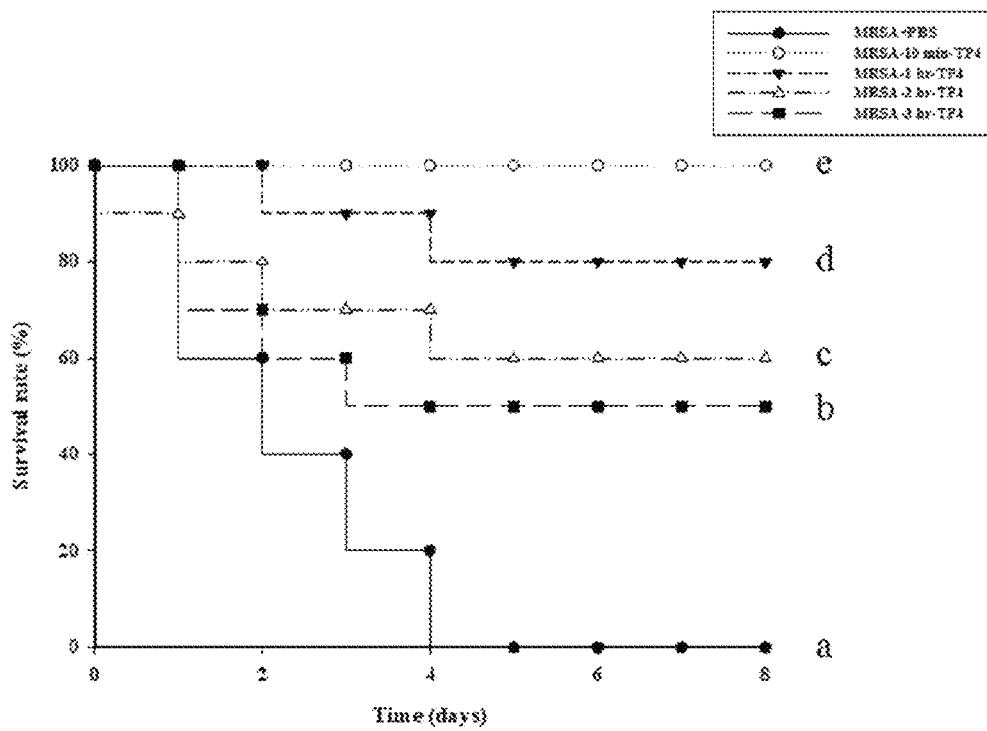

To determine the curative potential, mice were first injected with MRSA and then injected with TP4 (0.005 mg/g) 10, 60, 120, or 180 min later. At these injection times, the MRSA experimental groups exhibited survival rates of 100%, 80%, 60%, and 50%, respectively, see FIG. 7B. The survival rates of mice treated with TP4 were consistently greater than those of untreated mice (PBS-treated control mice). These data indicated that immediate application of TP4 (0.005 mg/g) is important to prevent severe infection.

2.15 Efficacy of TP4 on In Vivo Wound Closure

Figure 8A:
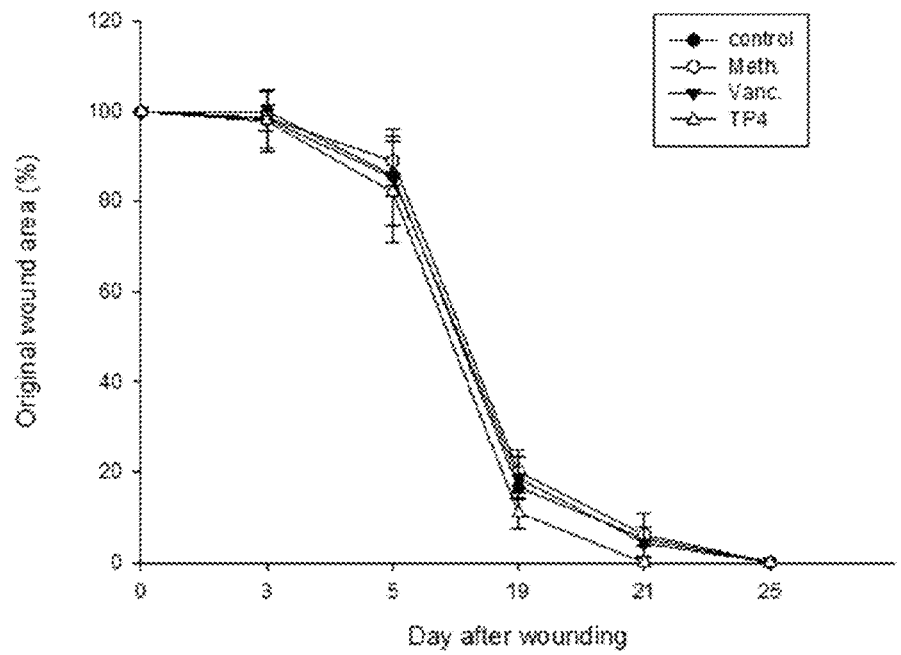
FIGS. 8A and 8B show the closure of clean and contaminated wounds; wherein the areas of full-thickness wounds (initially 1 cm in diameter) were measured from the time of wounding until closure.
Figure 8B:
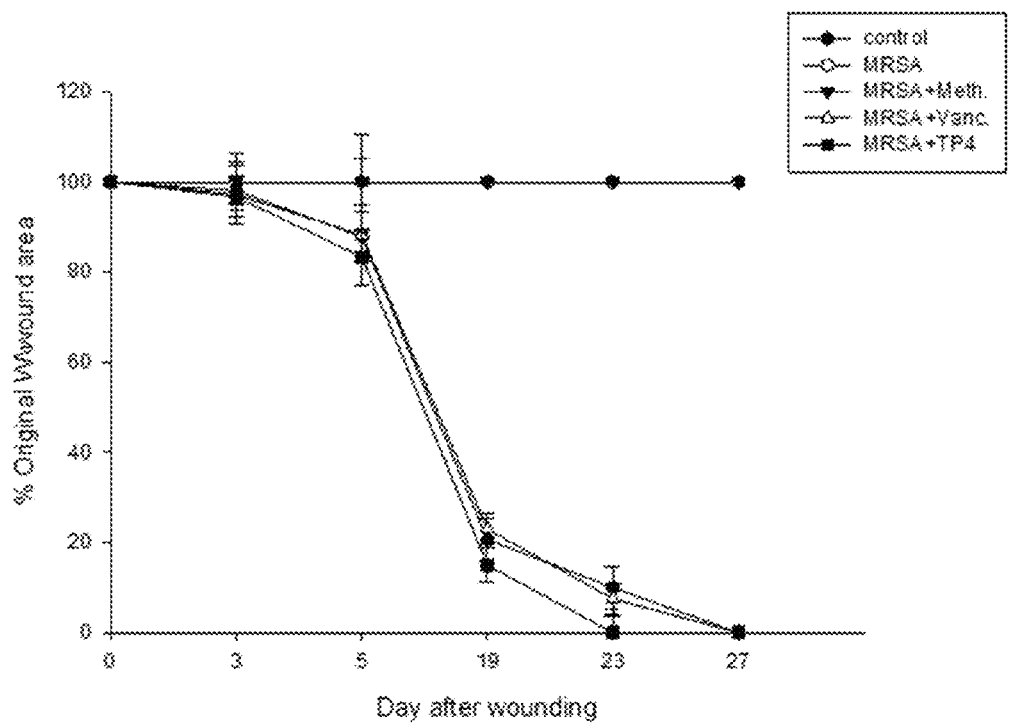

The effects of TP4 to promote healing of wounds was examined in an aseptic manner, see FIG. 8A. No statistical difference was observed between the areas of untreated wounds and Tegaderm™ or antibiotic-treated wounds, with all closing by day >25. This was not unexpected, as skin wounds heal efficiently in healthy mice, and it is unlikely that this process can be significantly improved. Treatment with vancomycin resulted in a similar wound closure time to the control, while wound closure was accelerated by treatment with TP4 alone. Such an increase in wound closure was not observed in uncontaminated wounds, suggesting that TP4 may facilitate wound recovery by combating infection. Unlike the uncontaminated wounds, wound size was largely unchanged after one week in all treatment groups, see FIG. 8B. However, both groups demonstrated full closure by the end of the 27th day.

2.16 TP4 Reduced Inflammation Cytokines

Figure 9A:
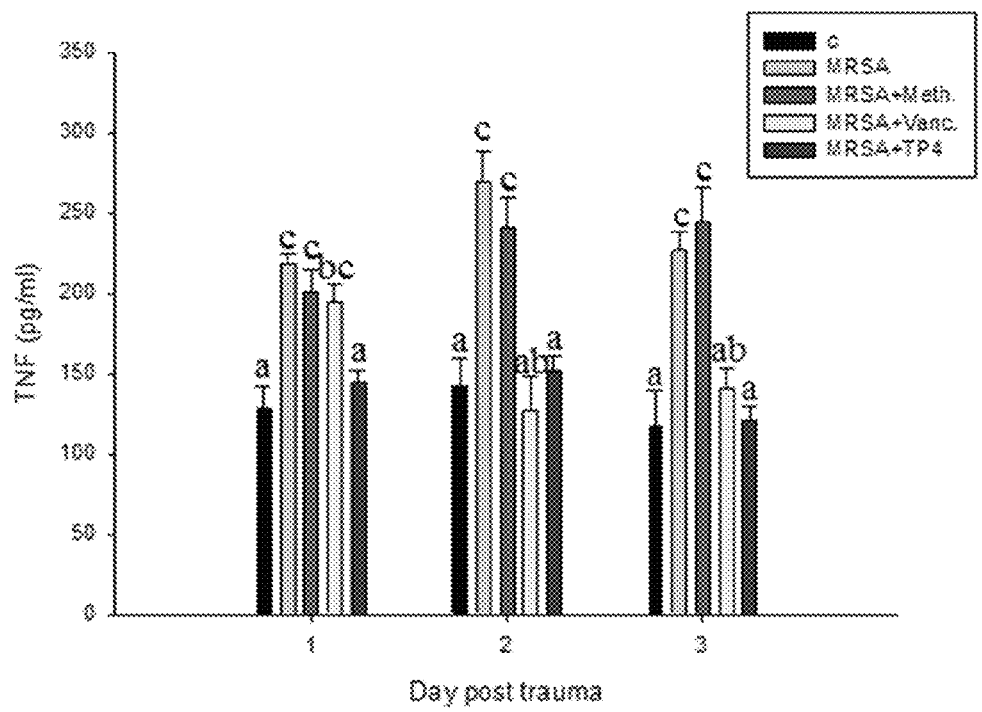
FIG. 9A-9C show that TP4 modulates MRSA mediated-induction of TNF, IL-6, and IL-1. A skin region of about 1 square centimeter was removed from the abdomen of non-anaesthetized mice, and the wound was infected with 50 ml of broth mix containing $10^6$ cfu of MRSA alone, or together with methicillin, vancomycin, or TP4. At different days post-infection: TNF (FIG. 9A), IL-6 (FIG. 9B), and IL-1 (FIG. 9C) were detected in serum by ELISA. (r=3; n=6.) Values with different letters show significant differences (P<0.05), as determined by ANOVA.
Figure 9B:
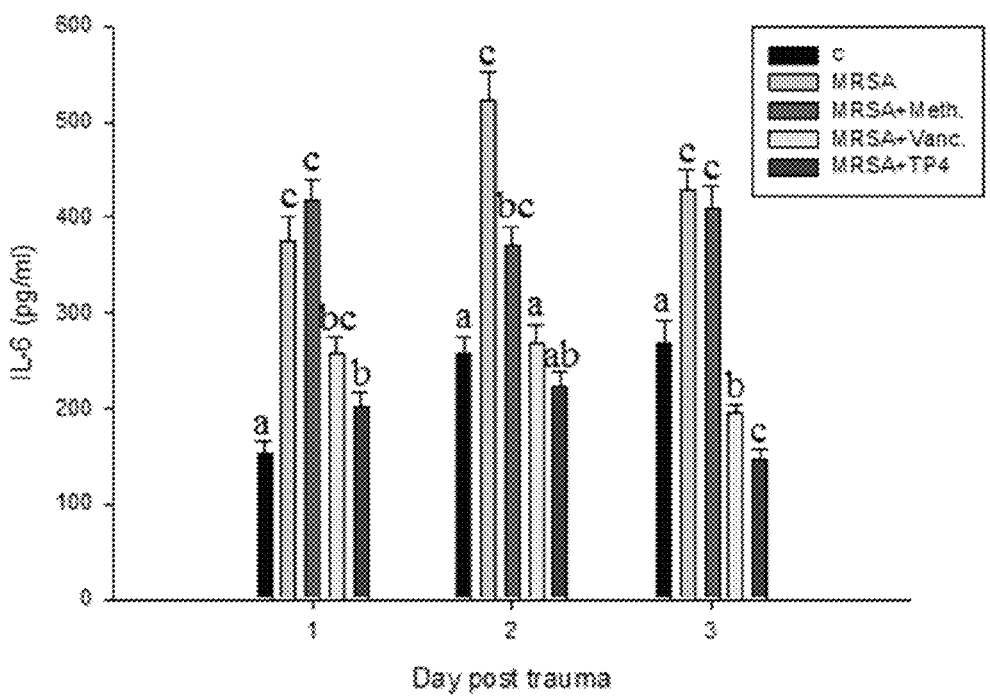
Figure 9C:
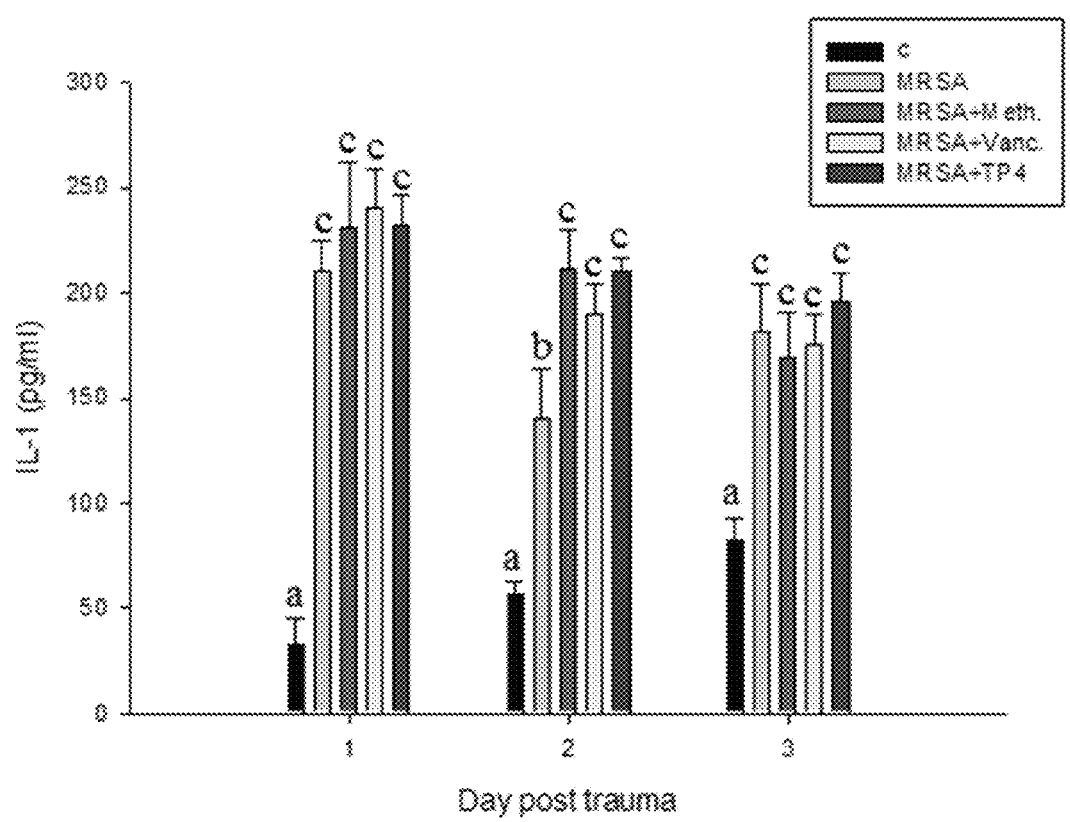

The direct antimicrobial activity of TP4 was examined. The ability of TP4 to modulate cytokines of mice was measured by ELISA, see FIG. 9A-9C. The proinflammatory cytokine IL-6 acts as a potent modulator of innate immunity, while the chemokine monocyte chemoattractant protein 1 (MCP-1) enhances the recruitment of monocytes and macrophages to tissue surrounding wounds. Serum chemokine and cytokine levels in MRSA-infected mice were evaluated at 3 days after treatment. MRSA-infected mice were used as a positive control to confirm cytokine activation. TP4 treatment decreased induction of IL-6 and TNF, compared to expression in the positive controls, see FIGS. 9A and 9B. In addition, the interleukin-1 (IL-1) protein is important for skin function, which enhances epidermal wound healing. A statistically significant enhancement of IL-1 in TP4-treated wounds was observed as compared with control wounds, see FIG. 9C.

Figure 10A:
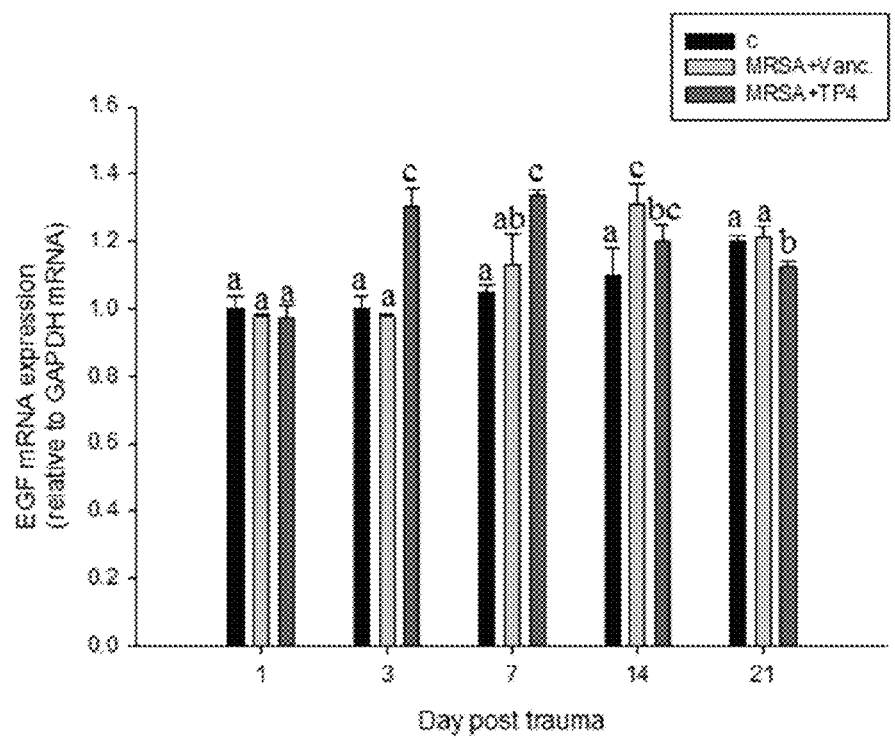
FIG. 10A-10C show that TP4 affected the expression profiles of cell proliferation genes in infected wounds of mice. Adult mice were infected with MRSA, and treated with TP4 or antibiotics, while controls were infected but untreated. On the indicated days, total RNA was isolated from the wound and reverse transcribed for use in real-time qPCR analysis of EGF (FIG. 10A), TGF-β (FIG. 10B), and VEGF (FIG. 10C) gene expression. (r=3; n=6.) Values with different letters show significant differences (P<0.05), as determined by ANOVA.
Figure 10B:
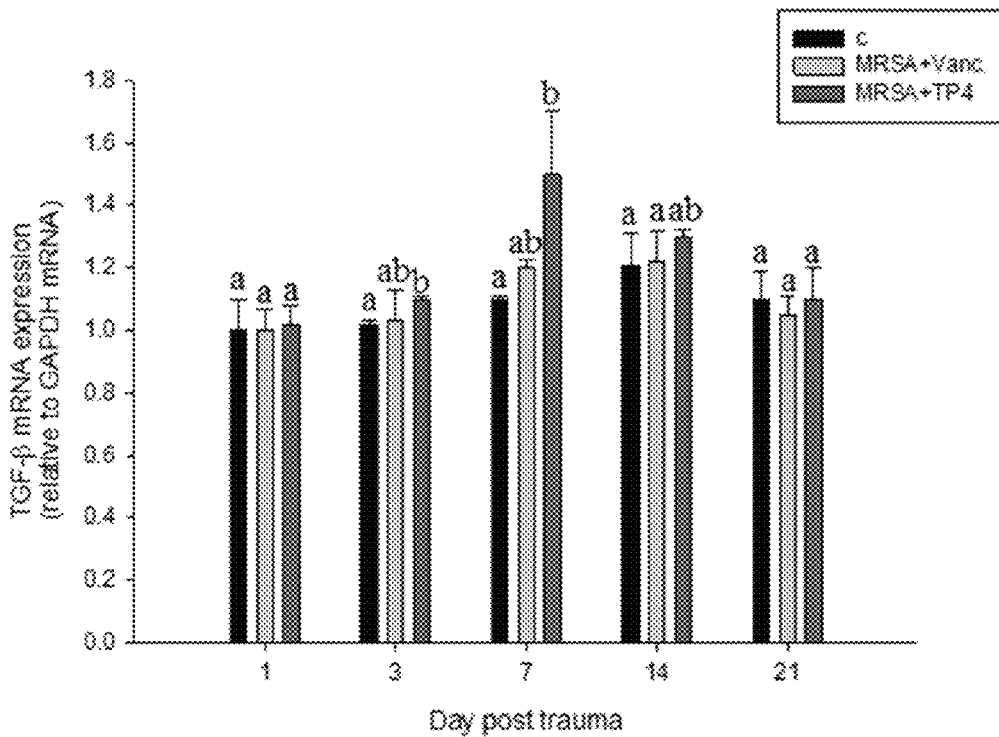
Figure 10C:
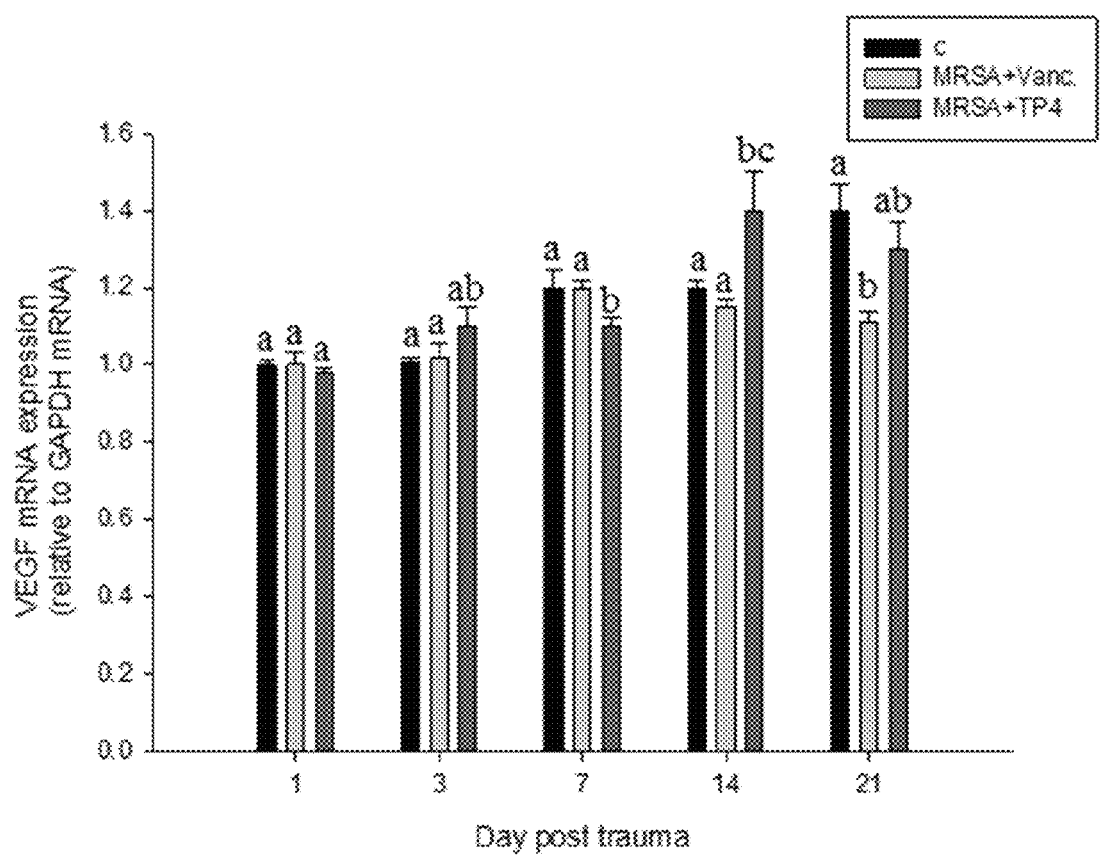

2.17 TP4 Alters Cell Proliferation Gene Expression Profiles in MRSA-Infected Mice During wound healing, monocytes began to replace neutrophils at 48 h, in order to remove wound debris; followed by the proliferation phase at 72 h, during which time several growth factors were induced. Epidermal growth factor (EGF), transforming growth factor beta (TGF-β), and vascular endothelial growth factor (VEGF) mediate cellular proliferation, regulate differentiation, and stimulate vasculogenesis and angiogenesis, respectively. To examine the expression profiles of cell proliferation genes in MRSA-infected mice treated with TP4, we subjected RNA, extracted from wound tissue of mice on days 1, 3, 7, 14, and 21 post-infection, to real-time RT-PCR. TP4 treatment enhanced gene expression of EGF (3 days), TGF (7 days), and VEGF (14 days) as compared to expression in control and vancomycin-treated mice, see FIG. 10A-10C. Mice were sacrificed on Days 7, 14, or 21 after wounding. Cryosections of wound sites were fixed in formaldehyde, and immunohistochemical analysis was performed using specific antibodies against VEGF. Histological examination of biopsies from TP4-treated wounds indicated complete and architecturally normal epidermal regeneration. This study suggests that topical administration of TP4 may be useful for the promotion of wound healing.

It was concluded that a wound agent should address all aspects of healing; it should not only promote tissue regeneration, but also induce hemostasis and limit microbial infection. These latter two processes are critical, as failure to accomplish these immediate and early steps prevents subsequent repair. It was demonstrated that TP4 both stimulated cell proliferation and exerts antibacterial activity. Also, TP4 appears to be involved in the regulation of certain processes of epithelial cells. Here, we observed that TP4 may modulate epidermal repair through control of fibroblast and keratinocyte proliferation and differentiation. We report that the effect of TP4 on keratinocyte cell line (HaCaT) and fibroblast cell line (Hs-68) proliferation may be mediated through activation of collagen I, collagen III, keratinocyte growth factor (KGF), and keratin 10 gene expression. In a clinically relevant model (suitable for elucidating the pathophysiology underlying the impairment of wound healing and for testing novel therapeutic agents), the utility of TP4 was confirmed. It was demonstrated that TP4 have anti-bacterial activity in vitro, TP4 exhibited strong antimicrobial activity in vivo, evident within 60 minutes of exposure. TP4 treatment caused a decrease in TNF and IL-6 at the site of infection on days 1, 2 and 3, as compared with the MRSA infection group. Although TP4 treatment caused a modest increase in IL-6 as compared to the control, this was lower than that induced by MRSA on day 1. The anti-inflammatory effect of TP4 may be due to contributions from several related mechanisms, including that of IL-10. Furthermore, TP4 reduced MRSA-induced TNF at the wound site on day 1. However, whether IL-1 directly regulates wound closure is unknown. Here, we show that IL-1 expression increases over time in MRSA-infected wounds in mice. TP4 was also observed to induce epidermal growth factor (EGF), transforming growth factor (TGF), and vascular endothelial growth factor (VEGF), which may enhance wound closure activity.

In conclusion, the use of TP4 may complement the use of antibiotics. Critically, TP4 is unlikely to induce resistance, compatible with the use of antibiotics, and does not have any apparent immunotoxic effects. Moreover, TP4 induces proliferation of epithelial cells, which may be due to altered gene expression of collagen I, collagen III, keratinocyte growth factor (KGF), and keratin. In addition to its host defense function and modulatory effect on the innate immune system, TP4 may play an important role in reducing the risk of infection.

The descriptions and claims as provided should be understood as of demonstrative purpose instead of limitative in any way to the scope of the present invention.

We claim:

1. A method for treating methicillin-resistant *Staphylococcus aureus* (MRSA) infection in a wound, comprising administering to a subject in need thereof a therapeutically effective amount of tilapia piscidin 3 (TP3) or tilapia piscidin 4 (TP4).

2. The method of claim 1, comprising administering to a subject in need thereof a therapeutically effective amount of TP3.

3. The method of claim 1, comprising administering to a subject in need thereof a therapeutically effective amount of TP4.

* * * * *

SEQUENCE LISTING

```
<160> NUMBER OF SEQ ID NOS: 43

<210> SEQ ID NO 1
<211> LENGTH: 28
<212> TYPE: DNA
<213> ORGANISM: Artificial Sequence
<220> FEATURE:
<223> OTHER INFORMATION: TP1 F primer

<400> SEQUENCE: 1
atgaagtctg ctgtgatctt tcttgtgc                                          28

<210> SEQ ID NO 2
<211> LENGTH: 23
<212> TYPE: DNA
<213> ORGANISM: Artificial Sequence
<220> FEATURE:
<223> OTHER INFORMATION: TP1 R primer
```

```
<400> SEQUENCE: 2
ctagtcaaat tcccgttgac gca                                        23

<210> SEQ ID NO 3
<211> LENGTH: 33
<212> TYPE: DNA
<213> ORGANISM: Artificial Sequence
<220> FEATURE:
<223> OTHER INFORMATION: TP2 F primer

<400> SEQUENCE: 3
atgaagtgtg ctgcagtatt tcttatgctg tcc                             33

<210> SEQ ID NO 4
<211> LENGTH: 26
<212> TYPE: DNA
<213> ORGANISM: Artificial Sequence
<220> FEATURE:
<223> OTHER INFORMATION: TP2 R primer

<400> SEQUENCE: 4
ctagtcaaaa ttaagtcgac gagggt                                     26

<210> SEQ ID NO 5
<211> LENGTH: 39
<212> TYPE: DNA
<213> ORGANISM: Artificial Sequence
<220> FEATURE:
<223> OTHER INFORMATION: TP3 F primer

<400> SEQUENCE: 5
atgaagtgca ccatgctgtt ccttgtgctg tcgatggtt                       39

<210> SEQ ID NO 6
<211> LENGTH: 23
<212> TYPE: DNA
<213> ORGANISM: Artificial Sequence
<220> FEATURE:
<223> OTHER INFORMATION: TP3 R primer

<400> SEQUENCE: 6
ctagttaaaa gcagcccttt ccc                                        23

<210> SEQ ID NO 7
<211> LENGTH: 39
<212> TYPE: DNA
<213> ORGANISM: Artificial Sequence
<220> FEATURE:
<223> OTHER INFORMATION: TP4 F primer

<400> SEQUENCE: 7
atgaagtgca ctatactgtt ccttgtgctg tcgatggtg                       39

<210> SEQ ID NO 8
<211> LENGTH: 28
<212> TYPE: DNA
<213> ORGANISM: Artificial Sequence
<220> FEATURE:
<223> OTHER INFORMATION: TP4 R primer

<400> SEQUENCE: 8
ctagttaaaa gcaactctct ctcgtttg                                   28
```

```
<210> SEQ ID NO 9
<211> LENGTH: 28
<212> TYPE: DNA
<213> ORGANISM: Artificial Sequence
<220> FEATURE:
<223> OTHER INFORMATION: TP5 F primer

<400> SEQUENCE: 9
atgaagtctg ccataatctt tcttgtat                                           28

<210> SEQ ID NO 10
<211> LENGTH: 27
<212> TYPE: DNA
<213> ORGANISM: Artificial Sequence
<220> FEATURE:
<223> OTHER INFORMATION: TP5 R primer

<400> SEQUENCE: 10
ctatgacatc acagcatctt caaattc                                            27

<210> SEQ ID NO 11
<211> LENGTH: 18
<212> TYPE: PRT
<213> ORGANISM: Oreochromis niloticus

<400> SEQUENCE: 11

Phe Asp Trp Asp Ser Val Leu Lys Gly Val Glu Gly Phe Val Arg Gly
 1               5                  10                  15

Tyr Phe

<210> SEQ ID NO 12
<211> LENGTH: 22
<212> TYPE: PRT
<213> ORGANISM: Oreochromis niloticus

<400> SEQUENCE: 12

Gly Glu Cys Ile Trp Asp Ala Ile Phe His Gly Ala Lys His Phe Leu
 1               5                  10                  15

His Arg Leu Val Asn Pro
            20

<210> SEQ ID NO 13
<211> LENGTH: 23
<212> TYPE: PRT
<213> ORGANISM: Oreochromis niloticus

<400> SEQUENCE: 13

Phe Ile His His Ile Ile Gly Gly Leu Phe Ser Val Gly Lys His Ile
 1               5                  10                  15

His Ser Leu Ile His Gly His
            20

<210> SEQ ID NO 14
<211> LENGTH: 25
<212> TYPE: PRT
<213> ORGANISM: Oreochromis niloticus

<400> SEQUENCE: 14

Phe Ile His His Ile Ile Gly Gly Leu Phe Ser Ala Gly Lys Ala Ile
 1               5                  10                  15

His Arg Leu Ile Arg Arg Arg Arg Arg
            20                  25
```

-continued

```
<210> SEQ ID NO 15
<211> LENGTH: 26
<212> TYPE: PRT
<213> ORGANISM: Oreochromis niloticus

<400> SEQUENCE: 15

Gln Leu Gln Gly Lys Gln Val Ser Gly Glu Val Val Gln Lys Val Leu
1               5                   10                  15

Gln Glu Leu Ile Gln Ser Val Ala Lys Pro
            20                  25

<210> SEQ ID NO 16
<211> LENGTH: 20
<212> TYPE: DNA
<213> ORGANISM: Artificial Sequence
<220> FEATURE:
<223> OTHER INFORMATION: TNF-a F primer

<400> SEQUENCE: 16
ggtgttcatc cattctctac                                          20

<210> SEQ ID NO 17
<211> LENGTH: 18
<212> TYPE: DNA
<213> ORGANISM: Artificial Sequence
<220> FEATURE:
<223> OTHER INFORMATION: TNF-a R primer

<400> SEQUENCE: 17
cccagcatct tgtgtttc                                            18

<210> SEQ ID NO 18
<211> LENGTH: 20
<212> TYPE: DNA
<213> ORGANISM: Artificial Sequence
<220> FEATURE:
<223> OTHER INFORMATION: IL-6 F primer

<400> SEQUENCE: 18
tccatccagt tgccttcttg                                          20

<210> SEQ ID NO 19
<211> LENGTH: 22
<212> TYPE: DNA
<213> ORGANISM: Artificial Sequence
<220> FEATURE:
<223> OTHER INFORMATION: IL-6 R primer

<400> SEQUENCE: 19
tttctcattt ccacgatttc cc                                       22

<210> SEQ ID NO 20
<211> LENGTH: 20
<212> TYPE: DNA
<213> ORGANISM: Artificial Sequence
<220> FEATURE:
<223> OTHER INFORMATION: CXCL5 F primer

<400> SEQUENCE: 20
ctgaccccag tgaagataag                                          20

<210> SEQ ID NO 21
<211> LENGTH: 20
<212> TYPE: DNA
<213> ORGANISM: Artificial Sequence
```

```
<220> FEATURE:
<223> OTHER INFORMATION: CXCL5 R primer

<400> SEQUENCE: 21
ccgatagtgt gacagatagg                                              20

<210> SEQ ID NO 22
<211> LENGTH: 19
<212> TYPE: DNA
<213> ORGANISM: Artificial Sequence
<220> FEATURE:
<223> OTHER INFORMATION: GADPH F primer

<400> SEQUENCE: 22
acaatgaata cggctacag                                               19

<210> SEQ ID NO 23
<211> LENGTH: 18
<212> TYPE: DNA
<213> ORGANISM: Artificial Sequence
<220> FEATURE:
<223> OTHER INFORMATION: GADPH R primer

<400> SEQUENCE: 23
ggtccagggt ttcttact                                                18

<210> SEQ ID NO 24
<211> LENGTH: 21
<212> TYPE: DNA
<213> ORGANISM: Artificial Sequence
<220> FEATURE:
<223> OTHER INFORMATION: GADPH F primer

<400> SEQUENCE: 24
cgctctctgc tcctcctgtt c                                            21

<210> SEQ ID NO 25
<211> LENGTH: 22
<212> TYPE: DNA
<213> ORGANISM: Artificial Sequence
<220> FEATURE:
<223> OTHER INFORMATION: GADPH R primer

<400> SEQUENCE: 25
ttgactccga ccttcacctt cc                                           22

<210> SEQ ID NO 26
<211> LENGTH: 22
<212> TYPE: DNA
<213> ORGANISM: Artificial Sequence
<220> FEATURE:
<223> OTHER INFORMATION: collagen I F primer

<400> SEQUENCE: 26
acagggcgac agaggcataa ag                                           22

<210> SEQ ID NO 27
<211> LENGTH: 19
<212> TYPE: DNA
<213> ORGANISM: Artificial Sequence
<220> FEATURE:
<223> OTHER INFORMATION: collagen I R primer

<400> SEQUENCE: 27
ccaggagcac cagcagagc                                               19
```

```
<210> SEQ ID NO 28
<211> LENGTH: 23
<212> TYPE: DNA
<213> ORGANISM: Artificial Sequence
<220> FEATURE:
<223> OTHER INFORMATION: collagen III F primer

<400> SEQUENCE: 28
tccaaagggt gacaagggtg aac                                              23

<210> SEQ ID NO 29
<211> LENGTH: 24
<212> TYPE: DNA
<213> ORGANISM: Artificial Sequence
<220> FEATURE:
<223> OTHER INFORMATION: collagen III R primer

<400> SEQUENCE: 29
aggaggacca ataggaccag tagg                                             24

<210> SEQ ID NO 30
<211> LENGTH: 23
<212> TYPE: DNA
<213> ORGANISM: Artificial Sequence
<220> FEATURE:
<223> OTHER INFORMATION: KGF F primer

<400> SEQUENCE: 30
gcaactgaac ttactacgaa ctg                                              23

<210> SEQ ID NO 31
<211> LENGTH: 23
<212> TYPE: DNA
<213> ORGANISM: Artificial Sequence
<220> FEATURE:
<223> OTHER INFORMATION: KGF R primer

<400> SEQUENCE: 31
tcattgacct cttcctatct gtg                                              23

<210> SEQ ID NO 32
<211> LENGTH: 21
<212> TYPE: DNA
<213> ORGANISM: Artificial Sequence
<220> FEATURE:
<223> OTHER INFORMATION: keratin10 F primer

<400> SEQUENCE: 32
ctgcgtaggg tgctggatga g                                                21

<210> SEQ ID NO 33
<211> LENGTH: 24
<212> TYPE: DNA
<213> ORGANISM: Artificial Sequence
<220> FEATURE:
<223> OTHER INFORMATION: keratin 10 R primer

<400> SEQUENCE: 33
ttcctcctcg tggttcttct tcag                                             24

<210> SEQ ID NO 34
<211> LENGTH: 19
<212> TYPE: DNA
<213> ORGANISM: Artificial Sequence
<220> FEATURE:
<223> OTHER INFORMATION: keratin 17 F primer
```

```
<400> SEQUENCE: 34
ctggctgctg atgacttcc                                                19

<210> SEQ ID NO 35
<211> LENGTH: 20
<212> TYPE: DNA
<213> ORGANISM: Artificial Sequence
<220> FEATURE:
<223> OTHER INFORMATION: keratin 17 R primer

<400> SEQUENCE: 35
cctcctcgtg gttcttcttc                                               20

<210> SEQ ID NO 36
<211> LENGTH: 20
<212> TYPE: DNA
<213> ORGANISM: Artificial Sequence
<220> FEATURE:
<223> OTHER INFORMATION: GADPH F primer

<400> SEQUENCE: 36
ctccaaggag taagaaaccc                                               20

<210> SEQ ID NO 37
<211> LENGTH: 20
<212> TYPE: DNA
<213> ORGANISM: Artificial Sequence
<220> FEATURE:
<223> OTHER INFORMATION: GADPH R primer

<400> SEQUENCE: 37
tggaaattgt gagggagatg                                               20

<210> SEQ ID NO 38
<211> LENGTH: 20
<212> TYPE: DNA
<213> ORGANISM: Artificial Sequence
<220> FEATURE:
<223> OTHER INFORMATION: EGF F primer

<400> SEQUENCE: 38
catatgtgat ggctactgct                                               20

<210> SEQ ID NO 39
<211> LENGTH: 20
<212> TYPE: DNA
<213> ORGANISM: Artificial Sequence
<220> FEATURE:
<223> OTHER INFORMATION: EGF R primer

<400> SEQUENCE: 39
ttaatgttcc tcagggaagc                                               20

<210> SEQ ID NO 40
<211> LENGTH: 20
<212> TYPE: DNA
<213> ORGANISM: Artificial Sequence
<220> FEATURE:
<223> OTHER INFORMATION: TGF-b F primer

<400> SEQUENCE: 40
cgtgctcttc ttcgacaata                                               20
```

```
<210> SEQ ID NO 41
<211> LENGTH: 20
<212> TYPE: DNA
<213> ORGANISM: Artificial Sequence
<220> FEATURE:
<223> OTHER INFORMATION: TGF-b R primer

<400> SEQUENCE: 41
aacatgaaca aacagtccct                                               20

<210> SEQ ID NO 42
<211> LENGTH: 20
<212> TYPE: DNA
<213> ORGANISM: Artificial Sequence
<220> FEATURE:
<223> OTHER INFORMATION: VEGF F primer

<400> SEQUENCE: 42
acctttggga agaagatgtc                                               20

<210> SEQ ID NO 43
<211> LENGTH: 20
<212> TYPE: DNA
<213> ORGANISM: Artificial Sequence
<220> FEATURE:
<223> OTHER INFORMATION: VEGF R primer

<400> SEQUENCE: 43
caatagaacc ctcgagtgag                                               20
```